(12) United States Patent
Kjoerling et al.

(10) Patent No.: US 12,296,028 B2
(45) Date of Patent: *May 13, 2025

(54) INTEGRATION OF HIGH FREQUENCY RECONSTRUCTION TECHNIQUES WITH REDUCED POST-PROCESSING DELAY

(71) Applicant: DOLBY INTERNATIONAL AB, Dublin (IE)

(72) Inventors: Kristofer Kjoerling, Solna (SE); Lars Villemoes, Järfälla (SE); Heiko Purnhagen, Sundbyberg (SE); Per Ekstrand, Saltsjöbaden (SE)

(73) Assignee: DOLBY INTERNATIONAL AB, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/982,254

(22) Filed: Dec. 16, 2024

(65) Prior Publication Data
US 2025/0118313 A1    Apr. 10, 2025

Related U.S. Application Data

(63) Continuation of application No. 18/417,902, filed on Jan. 19, 2024, now Pat. No. 12,243,543, which is a (Continued)

(51) Int. Cl.
*G10L 19/18*    (2013.01)
*A61B 5/055*    (2006.01)
(Continued)

(52) U.S. Cl.
CPC .............. *A61K 49/10* (2013.01); *A61B 5/055* (2013.01); *G01R 33/5601* (2013.01);
(Continued)

(58) Field of Classification Search
CPC .............................. G10L 19/18; G10L 21/038
See application file for complete search history.

(56) References Cited

U.S. PATENT DOCUMENTS 6,680,972 B1    1/2004    Liljeryd
7,283,955 B2   10/2007    Liljeryd
(Continued)

FOREIGN PATENT DOCUMENTS

CN    1498456 A     5/2004
CN    101458930     6/2009
(Continued)

OTHER PUBLICATIONS

Manfred Lutzky et al., A guideline to audio codec delay, May 2004, Audio Engineering Society (Year: 2004).*

(Continued)

*Primary Examiner* — Richemond Dorvil
*Assistant Examiner* — Ethan Daniel Kim

(57) ABSTRACT

A method for decoding an encoded audio bitstream is disclosed. The method includes receiving the encoded audio bitstream and decoding the audio data to generate a decoded lowband audio signal. The method further includes extracting high frequency reconstruction metadata and filtering the decoded lowband audio signal with an analysis filterbank to generate a filtered lowband audio signal. The method also includes extracting a flag indicating whether either spectral translation or harmonic transposition is to be performed on the audio data and regenerating a highband portion of the audio signal using the filtered lowband audio signal and the high frequency reconstruction metadata in accordance with the flag. The high frequency regeneration is performed as a post-processing operation with a delay of 3010 samples per audio channel.

5 Claims, 2 Drawing Sheets

Related U.S. Application Data continuation of application No. 18/157,644, filed on Jan. 20, 2023, now Pat. No. 11,908,486, which is a continuation of application No. 17/050,664, filed as application No. PCT/US2019/029144 on Apr. 25, 2019, now Pat. No. 11,562,759.

(51) Int. Cl.
 *A61K 49/10* (2006.01)
 *G01R 33/56* (2006.01)
 *G01R 33/563* (2006.01)
 *G10L 21/038* (2013.01)

(52) U.S. Cl.
 CPC ........ *G01R 33/56366* (2013.01); *G10L 19/18* (2013.01); *G10L 21/038* (2013.01)

(56) References Cited

U.S. PATENT DOCUMENTS

| | | | |
|---|---|---|---|
| 7,447,631 | B2 | 11/2008 | Truman |
| 8,260,609 | B2* | 9/2012 | Rajendran ............... G10L 19/24 704/208 |
| 8,515,768 | B2 | 8/2013 | Baumgarte |
| 8,971,551 | B2 | 3/2015 | Ekstrand |
| 9,047,875 | B2 | 6/2015 | Gao |
| 2002/0103637 | A1* | 8/2002 | Henn ................... G10L 21/038 704/E19.041 |
| 2004/0042557 | A1 | 3/2004 | Kabel |
| 2004/0225505 | A1 | 11/2004 | Andersen |
| 2005/0096917 | A1 | 5/2005 | Kjorling |
| 2006/0098827 | A1 | 5/2006 | Paddock |
| 2008/0027717 | A1 | 1/2008 | Rajendran |
| 2008/0071523 | A1* | 3/2008 | Oshikiri ................ G10L 19/018 704/E19.009 |
| 2008/0071550 | A1 | 3/2008 | Oh |
| 2009/0326929 | A1 | 12/2009 | Kjörling |
| 2011/0054885 | A1 | 3/2011 | Nagel |
| 2011/0054911 | A1 | 3/2011 | Baumgarte |
| 2011/0173006 | A1 | 7/2011 | Nagel |
| 2011/0282675 | A1 | 11/2011 | Nagel |
| 2011/0302230 | A1 | 12/2011 | Ekstrand |
| 2011/0305352 | A1 | 12/2011 | Villemoes |
| 2012/0016667 | A1 | 1/2012 | Gao |
| 2012/0065983 | A1 | 3/2012 | Ekstrand |
| 2012/0158409 | A1 | 6/2012 | Nagel |
| 2012/0213378 | A1* | 8/2012 | Liljeryd ................ G10L 19/265 381/22 |
| 2012/0278088 | A1 | 11/2012 | Villemoes |
| 2012/0328124 | A1 | 12/2012 | Kjoerling |
| 2013/0051571 | A1 | 2/2013 | Nagel |
| 2013/0058498 | A1 | 3/2013 | Disch |
| 2013/0197920 | A1* | 8/2013 | Lesso ................... H04L 25/4902 704/500 |
| 2016/0099005 | A1 | 4/2016 | Liljeryd |
| 2016/0140980 | A1* | 5/2016 | Disch ................... G10L 19/0212 |
| 2016/0284359 | A1* | 9/2016 | Niedermeier ........... G10L 19/20 |
| 2017/0070211 | A1* | 3/2017 | Ekstrand ............... G10L 19/008 |
| 2017/0180905 | A1 | 6/2017 | Purnhagen |
| 2017/0206911 | A1 | 7/2017 | Ekstrand |
| 2018/0025737 | A1 | 1/2018 | Villemoes |
| 2018/0075865 | A1 | 3/2018 | Villemoes |
| 2019/0005969 | A1* | 1/2019 | Dick ..................... G10L 19/035 |
| 2020/0020349 | A1* | 1/2020 | Disch ..................... G10L 19/03 |

FOREIGN PATENT DOCUMENTS

| | | |
|---|---|---|
| CN | 101140759 B | 5/2010 |
| CN | 101925950 A | 12/2010 |
| CN | 102318004 A | 1/2012 |
| CN | 102473414 | 5/2012 |
| CN | 102842337 A | 12/2012 |
| CN | 102985970 | 3/2013 |
| CN | 103038819 | 4/2013 |
| CN | 103124354 A | 5/2013 |
| CN | 102282612 B | 7/2013 |
| CN | 103248887 A | 8/2013 |
| CN | 103632678 A | 3/2014 |
| CN | 102449692 B | 5/2014 |
| CN | 103971699 | 8/2014 |
| CN | 104318930 | 1/2015 |
| CN | 103559891 B | 5/2016 |
| CN | 107408391 A | 11/2017 |
| CN | 107925388 A | 4/2018 |
| CN | 107430867 B | 12/2018 |
| CN | 112204659 B | 12/2021 |
| EP | 1540941 | 6/2005 |
| IN | 201737001634 A | 5/2017 |
| JP | 2010-020251 | 1/2010 |
| JP | 2011-527447 | 10/2011 |
| JP | 2012141631 A | 7/2012 |
| JP | 2012-531632 | 12/2012 |
| JP | 2013-516652 | 5/2013 |
| JP | 2013-521536 | 6/2013 |
| JP | 2013-521538 | 6/2013 |
| JP | 2015111277 A | 6/2015 |
| JP | 2017062483 A | 3/2017 |
| RU | 2530254 | 10/2014 |
| RU | 2614573 C2 | 3/2017 |
| RU | 2648947 C2 | 3/2018 |
| TW | 200926148 A | 6/2009 |
| TW | 201547195 A | 12/2015 |
| WO | 2013036348 A2 | 3/2013 |
| WO | 2013068587 A2 | 5/2013 |
| WO | 2013127801 A1 | 9/2013 |
| WO | 2016146492 | 9/2016 |
| WO | 2016147015 A1 | 9/2016 |
| WO | 2016149015 A1 | 9/2016 |
| WO | 2019148112 | 8/2019 |

OTHER PUBLICATIONS

U Christof Fersch et al., Coding of Moving Pictures and Audio, Apr. 2017, Fraunhofer IIS, Dolby (Year: 2017).*

Bhatt, "A Novel Approach for Artificial Bandwidth Extension of Speech Signals by LPC technique over proposed GSM FR NB coder using High Band Feature Extraction and Various Extension of Excitation Methods", Int J. Speech Technol, 18:57-64, 2015, DOI 10-1007/s10772-014-9249-1, pp. 57-64 (Year: 2015).

Christof Fersch et al., Coding of Moving Pictures and Audio, Apr. 2017, Fraunhofer IIS, Dolby (Year: 2017).

Fersch, C. et al "Proposed Updates to MPEG-4" ISO/IEC JTC1/SC29/WG11 MPEG2017, Apr. 2017.

Final text of ISO/IEC 14496-3:2009/Amd. 7, SBR Enhancements, 122. MPEG Meeting; Apr. 16, 2018-Apr. 20, 2018; San Diego; (Motion Picture Expert Group or ISO/IEC JTC1 /SC29/WG11 ), No. n17620, Apr. 21, 2018, XP030262043.

Gayer, M. et al "A Guideline to Audio Codec Delay" AES Convention, May 1, 2004, paper No. 6062.

Hotho et al "A Backward-Compatible Multichannel Audio Codec", IEEE Trans. On Audio, Speech, and Language Proc., vol. 16, No. 1, pp. 83-93, Jan. 2008.

ISO/I EC 14496-3, Information Technology—Coding of audio-visual objects, Part 3: Audio, 3rd Edition, p. 1-1178, Dec. 1, 2005.

ISO/IEC 14496-3 "Information Technology—Coding of Audio-Visual Objects" Part 3: Audio, Fourth Edition Sep. 2009.

ISO/IEC 23003-3:2012 "Information Technology—MPEG Audio Technologies—Part 3: Unified Speech and Audio Coding". Apr. 1, 2012.

ISO/IEC 23003-3:201x/DIS of Unified Speech and Audio Coding, 95. MPE G Meeting; Jan. 24, 2011-Jan. 28, 2011; Daegu; (Motion Picture Expert Group or ISO/IEC JTC1/SC29/WG11), No. N1 1863, Feb. 9, 2011, XP030018356.

ISO/IEC JTC 1/SC29/WG11 N12013, "Coding of Moving Pictures and Audio", Mar. 2011, Geneva, 274 pages, Mar. 2011.

ISO23003, "Information Technology—MPEG audio technologies—Part 3: Unified Speech and Audio Coding", ISO/IEC FDIS 23003-3:2011 (E), Sep. 20, p. 1-291 (Year: 2011).

(56) References Cited

OTHER PUBLICATIONS

Lutzy, et al "A guideline to Audio Codec Delay" AES Convention Paper 6062, 116th Convention, pp. 1-10, May 8-11, 2004.
Marc, G. et al "A Guideline to Audio Codec Delay" AES Convention 116, May 2004.
Nagel et al, "A Phase Vocoder Driven Bandwidth Extension Method with Novel Transient Handling For Audio Codecs", AES Convention Paper 7711, Presented at the 126th Convention, p. 1-8, Munich, Germany, May 7-10, 2009.
Nagel, F. et al "A Harmonic Bandwidth Extension Method for Audio Codecs" IEEE International Conference on Acoustics, Speech and Signal Processing, Jan. 2009, pp. 145-148.
Neuendorf et al, "MPEG Unified Speech and Audio Coding—The ISO/MPEG Standard for High-Efficiency Audio Coding of All Content Types", AES Convention Paper 8654, the 132nd Convention, p. 1-22, Budapest, Hungary, Apr. 26-29, 2012.
Overview of Spectral Band Replication in Audio Coding, Liu Dongbing, Du Weitao, Yang Zhanxin; Journal of Liaoning University (Natural Science Edition). Dec. 31, 2011.
Takeshi Norimatsu et al., Acoustic signal coding that integrates voice and musical tones, Journal of the Acoustical Society of Japan, Mar. 2012, vol. 68, No. 3, p. 123-128.
Testing and Analysis of Spectral Band Replication Technology, Guo Qingwei, Zhang Haibo, Ma Hongfei, Quality Engineering. Dec. 20, 2007.
Lin Shengyi, et al., The Approach of Speed Bandwidth Expansion Based on Linear Source-Filter, Automation and Information Engineering, Issue 1.

\* cited by examiner

INTEGRATION OF HIGH FREQUENCY RECONSTRUCTION TECHNIQUES WITH REDUCED POST-PROCESSING DELAY

CROSS-REFERENCE TO RELATED APPLICATIONS

This is a continuation application of U.S. patent application Ser. No. 18/417,902, filed Jan. 19, 2024, which is a continuation application of U.S. patent application Ser. No. 18/157,644, filed Jan. 20, 2023, now a U.S. Pat. No. 11,908,486, which is a continuation application of U.S. patent application Ser. No. 17/050,664, filed Oct. 26, 2020 (now Issued U.S. Pat. No. 11,562,759), which is the 371 national stage of PCT Application No PCT/US2019/029144 filed Apr. 25, 2019, which claims priority to U.S. Provisional Patent Application No. 62/662,296, filed 25 Apr. 2018, which is incorporated herein by reference in their entirety.

TECHNICAL FIELD

Embodiments pertain to audio signal processing, and more specifically, to encoding, decoding, or transcoding of audio bitstreams with control data specifying that either a base form of high frequency reconstruction ("HFR") or an enhanced form of HFR is to be performed on the audio data.

BACKGROUND OF THE INVENTION

A typical audio bitstream includes both audio data (e.g., encoded audio data) indicative of one or more channels of audio content, and metadata indicative of at least one characteristic of the audio data or audio content. One well known format for generating an encoded audio bitstream is the MPEG-4 Advanced Audio Coding (AAC) format, described in the MPEG standard ISO/IEC 14496-3:2009. In the MPEG-4 standard, AAC denotes "advanced audio coding" and HE-AAC denotes "high-efficiency advanced audio coding."

The MPEG-4 AAC standard defines several audio profiles, which determine which objects and coding tools are present in a complaint encoder or decoder. Three of these audio profiles are (1) the AAC profile, (2) the HE-AAC profile, and (3) the HE-AAC v2 profile. The AAC profile includes the AAC low complexity (or "AAC-LC") object type. The AAC-LC object is the counterpart to the MPEG-2 AAC low complexity profile, with some adjustments, and includes neither the spectral band replication ("SBR") object type nor the parametric stereo ("PS") object type. The HE-AAC profile is a superset of the AAC profile and additionally includes the SBR object type. The HE-AAC v2 profile is a superset of the HE-AAC profile and additionally includes the PS object type.

The SBR object type contains the spectral band replication tool, which is an important high frequency reconstruction ("HFR") coding tool that significantly improves the compression efficiency of perceptual audio codecs. SBR reconstructs the high frequency components of an audio signal on the receiver side (e.g., in the decoder). Thus, the encoder needs to only encode and transmit low frequency components, allowing for a much higher audio quality at low data rates. SBR is based on replication of the sequences of harmonics, previously truncated in order to reduce data rate, from the available bandwidth limited signal and control data obtained from the encoder. The ratio between tonal and noise-like components is maintained by adaptive inverse filtering as well as the optional addition of noise and sinusoidals. In the MPEG-4 AAC standard, the SBR tool performs spectral patching (also called linear translation or spectral translation), in which a number of consecutive Quadrature Mirror Filter (QMF) subbands are copied (or "patched" or) from a transmitted lowband portion of an audio signal to a highband portion of the audio signal, which is generated in the decoder.

Spectral patching or linear translation may not be ideal for certain audio types, such as musical content with relatively low cross over frequencies. Therefore, techniques for improving spectral band replication are needed.

Brief Description of Embodiments of the Invention

A first class of embodiments relates to a method for decoding an encoded audio bitstream is disclosed. The method includes receiving the encoded audio bitstream and decoding the audio data to generate a decoded lowband audio signal. The method further includes extracting high frequency reconstruction metadata and filtering the decoded lowband audio signal with an analysis filterbank to generate a filtered lowband audio signal. The method further includes extracting a flag indicating whether either spectral translation or harmonic transposition is to be performed on the audio data and regenerating a highband portion of the audio signal using the filtered lowband audio signal and the high frequency reconstruction metadata in accordance with the flag. Finally, the method includes combining the filtered lowband audio signal and the regenerated highband portion to form a wideband audio signal.

A second class of embodiments relates to an audio decoder for decoding an encoded audio bitstream. The decoder includes an input interface for receiving the encoded audio bitstream where the encoded audio bitstream includes audio data representing a lowband portion of an audio signal and a core decoder for decoding the audio data to generate a decoded lowband audio signal. The decoder also includes a demultiplexer for extracting from the encoded audio bitstream high frequency reconstruction metadata where the high frequency reconstruction metadata includes operating parameters for a high frequency reconstruction process that linearly translates a consecutive number of subbands from a lowband portion of the audio signal to a highband portion of the audio signal and an analysis filterbank for filtering the decoded lowband audio signal to generate a filtered lowband audio signal. The decoder further includes a demultiplexer for extracting from the encoded audio bitstream a flag indicating whether either linear translation or harmonic transposition is to be performed on the audio data and a high frequency regenerator for regenerating a highband portion of the audio signal using the filtered lowband audio signal and the high frequency reconstruction metadata in accordance with the flag. Finally, the decoder includes a synthesis filterbank for combining the filtered lowband audio signal and the regenerated highband portion to form a wideband audio signal.

Other classes of embodiments relate to encoding and transcoding audio bitstreams containing metadata identifying whether enhanced spectral band replication (eSBR) processing is to be performed.

NOTATION AND NOMENCLATURE

Figure 1:
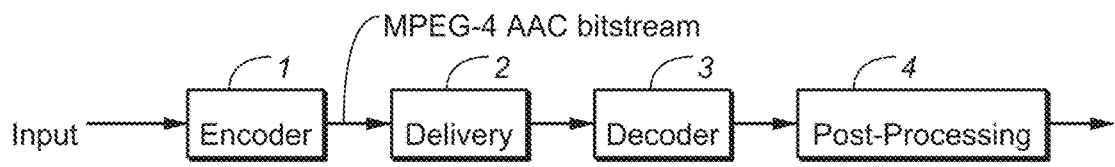
FIG. 1 is a block diagram of an embodiment of a system which may be configured to perform an embodiment of the inventive method.

Throughout this disclosure, including in the claims, the expression performing an operation "on" a signal or data (e.g., filtering, scaling, transforming, or applying gain to, the signal or data) is used in a broad sense to denote performing the operation directly on the signal or data, or on a processed version of the signal or data (e.g., on a version of the signal that has undergone preliminary filtering or pre-processing prior to performance of the operation thereon).

Throughout this disclosure, including in the claims, the expression "audio processing unit" or "audio processor" is used in a broad sense, to denote a system, device, or apparatus, configured to process audio data. Examples of audio processing units include, but are not limited to encoders, transcoders, decoders, codecs, pre-processing systems, post-processing systems, and bitstream processing systems (sometimes referred to as bitstream processing tools). Virtually all consumer electronics, such as mobile phones, televisions, laptops, and tablet computers, contain an audio processing unit or audio processor.

Throughout this disclosure, including in the claims, the term "couples" or "coupled" is used in a broad sense to mean either a direct or indirect connection. Thus, if a first device couples to a second device, that connection may be through a direct connection, or through an indirect connection via other devices and connections. Moreover, components that are integrated into or with other components are also coupled to each other.

DETAILED DESCRIPTION OF EMBODIMENTS OF THE INVENTION

The MPEG-4 AAC standard contemplates that an encoded MPEG-4 AAC bitstream includes metadata indicative of each type of high frequency reconstruction ("HFR") processing to be applied (if any is to be applied) by a decoder to decode audio content of the bitstream, and/or which controls such HFR processing, and/or is indicative of at least one characteristic or parameter of at least one HFR tool to be employed to decode audio content of the bitstream. Herein, we use the expression "SBR metadata" to denote metadata of this type which is described or mentioned in the MPEG-4 AAC standard for use with spectral band replication ("SBR"). As appreciated by one skilled in the art, SBR is a form of HFR.

SBR is preferably used as a dual-rate system, with the underlying codec operating at half the original sampling-rate, while SBR operates at the original sampling rate. The SBR encoder works in parallel with the underlying core codec, albeit at a higher sampling-rate. Although SBR is mainly a post process in the decoder, important parameters are extracted in the encoder in order to ensure the most accurate high frequency reconstruction in the decoder. The encoder estimates the spectral envelope of the SBR range for a time and frequency range/resolution suitable for the current input signal segments characteristics. The spectral envelope is estimated by a complex QMF analysis and subsequent energy calculation. The time and frequency resolutions of the spectral envelopes can be chosen with a high level of freedom, in order to ensure the best suited time frequency resolution for the given input segment. The envelope estimation needs to consider that a transient in the original, mainly situated in the high frequency region (for instance a high-hat), will be present to a minor extent in the SBR generated highband prior to envelope adjustment, since the highband in the decoder is based on the low band where the transient is much less pronounced compared to the highband. This aspect imposes different requirements for the time frequency resolution of the spectral envelope data, compared to ordinary spectral envelope estimation as used in other audio coding algorithms.

Apart from the spectral envelope, several additional parameters are extracted representing spectral characteristics of the input signal for different time and frequency regions. Since the encoder naturally has access to the original signal as well as information on how the SBR unit in the decoder will create the high-band, given the specific set of control parameters, it is possible for the system to handle situations where the lowband constitutes a strong harmonic series and the highband, to be recreated, mainly constitutes random signal components, as well as situations where strong tonal components are present in the original highband without counterparts in the lowband, upon which the highband region is based. Furthermore, the SBR encoder works in close relation to the underlying core codec to assess which frequency range should be covered by SBR at a given time. The SBR data is efficiently coded prior to transmission by exploiting entropy coding as well as channel dependencies of the control data, in the case of stereo signals.

The control parameter extraction algorithms typically need to be carefully tuned to the underlying codec at a given bitrate and a given sampling rate. This is due to the fact that a lower bitrate, usually implies a larger SBR range compared to a high bitrate, and different sampling rates correspond to different time resolutions of the SBR frames.

An SBR decoder typically includes several different parts. It comprises a bitstream decoding module, a high frequency reconstruction (HFR) module, an additional high frequency components module, and an envelope adjuster module. The system is based around a complex valued QMF filterbank (for high-quality SBR) or a real-valued QMF filterbank (for low-power SBR). Embodiments of the invention are applicable to both high-quality SBR and low-power SBR. In the bitstream extraction module, the control data is read from the bitstream and decoded. The time frequency grid is obtained for the current frame, prior to reading the envelope data from the bitstream. The underlying core decoder decodes the audio signal of the current frame (albeit at the lower sampling rate) to produce time-domain audio samples. The resulting frame of audio data is used for high frequency reconstruction by the HFR module. The decoded lowband signal is then analyzed using a QMF filterbank. The high frequency reconstruction and envelope adjustment is subsequently performed on the subband samples of the QMF filterbank. The high frequencies are reconstructed from the low-band in a flexible way, based on the given control parameters. Furthermore, the reconstructed highband is adaptively filtered on a subband channel basis according to the control data to ensure the appropriate spectral characteristics of the given time/frequency region.

The top level of an MPEG-4 AAC bitstream is a sequence of data blocks ("raw_data_block" elements), each of which is a segment of data (herein referred to as a "block") that contains audio data (typically for a time period of 1024 or 960 samples) and related information and/or other data. Herein, we use the term "block" to denote a segment of an MPEG-4 AAC bitstream comprising audio data (and corresponding metadata and optionally also other related data) which determines or is indicative of one (but not more than one) "raw_data_block" element.

Each block of an MPEG-4 AAC bitstream can include a number of syntactic elements (each of which is also materialized in the bitstream as a segment of data). Seven types of such syntactic elements are defined in the MPEG-4 AAC standard. Each syntactic element is identified by a different value of the data element "id_syn_ele." Examples of syntactic elements include a "single_channel_element ( )" a "channel_pair_element ( )" and a "fill_element ( )" A single channel element is a container including audio data of a single audio channel (a monophonic audio signal). A channel pair element includes audio data of two audio channels (that is, a stereo audio signal).

A fill element is a container of information including an identifier (e.g., the value of the above-noted element "id_syn_ele") followed by data, which is referred to as "fill data." Fill elements have historically been used to adjust the instantaneous bit rate of bitstreams that are to be transmitted over a constant rate channel. By adding the appropriate amount of fill data to each block, a constant data rate may be achieved.

In accordance with embodiments on the invention, the fill data may include one or more extension payloads that extend the type of data (e.g., metadata) capable of being transmitted in a bitstream. A decoder that receives bitstreams with fill data containing a new type of data may optionally be used by a device receiving the bitstream (e.g., a decoder) to extend the functionality of the device. Thus, as can be appreciated by one skilled in the art, fill elements are a special type of data structure and are different from the data structures typically used to transmit audio data (e.g., audio payloads containing channel data).

In some embodiments of the invention, the identifier used to identify a fill element may consist of a three bit unsigned integer transmitted most significant bit first ("uimsbf") having a value of 0×6. In one block, several instances of the same type of syntactic element (e.g., several fill elements) may occur.

Another standard for encoding audio bitstreams is the MPEG Unified Speech and Audio Coding (USAC) standard (ISO/IEC 23003-3:2012). The MPEG USAC standard describes encoding and decoding of audio content using spectral band replication processing (including SBR processing as described in the MPEG-4 AAC standard, and also including other enhanced forms of spectral band replication processing). This processing applies spectral band replication tools (sometimes referred to herein as "enhanced SBR tools" or "eSBR tools") of an expanded and enhanced version of the set of SBR tools described in the MPEG-4 AAC standard. Thus, eSBR (as defined in USAC standard) is an improvement to SBR (as defined in MPEG-4 AAC standard).

Herein, we use the expression "enhanced SBR processing" (or "eSBR processing") to denote spectral band replication processing using at least one eSBR tool (e.g., at least one eSBR tool which is described or mentioned in the MPEG USAC standard) which is not described or mentioned in the MPEG-4 AAC standard. Examples of such eSBR tools are harmonic transposition and QMF-patching additional pre-processing or "pre-flattening."

A harmonic transposer of integer order T maps a sinusoid with frequency ω into a sinusoid with frequency Tω, while preserving signal duration. Three orders, T=2, 3, 4, are typically used in sequence to produce each part of the desired output frequency range using the smallest possible transposition order. If output above the fourth order transposition range is required, it may be generated by frequency shifts. When possible, near critically sampled baseband time domains are created for the processing to minimize computational complexity.

The harmonic transposer may either be QMF or DFT based. When using the QMF based harmonic transposer, the bandwidth extension of the core coder time-domain signal is carried out entirely in the QMF domain, using a modified phase-vocoder structure, performing decimation followed by time stretching for every QMF subband. Transposition using several transpositions factors (e.g., T=2, 3, 4) is carried out in a common QMF analysis/synthesis transform stage. Since the QMF based harmonic transposer does not feature signal adaptive frequency domain oversampling, the corresponding flag in the bitstream (sbrOversamplingFlag [ch]) may be ignored.

When using the DFT based harmonic transposer, the factor 3 and 4 transposers (3rd and 4th order transposers) are preferably integrated into the factor 2 transposer (2nd order transposer) by means of interpolation to reduce complexity. For each frame (corresponding to coreCoderFrameLength core coder samples), the nominal "full size" transform size of the transposer is first determined by the signal adaptive frequency domain oversampling flag (sbrOversamplingFlag [ch]) in the bitstream.

When sbrPatchingMode==1, indicating that linear transposition is to be used to generate the highband, an additional step may be introduced to avoid discontinuities in the shape of the spectral envelope of the high frequency signal being input to the subsequent envelope adjuster. This improves the operation of the subsequent envelope adjustment stage, resulting in a highband signal that is perceived to be more stable. The operation of the additional preprocessing is beneficial for signal types where the coarse spectral envelope of the low band signal being used for high frequency reconstruction displays large variations in level. However, the value of the bitstream element may be determined in the encoder by applying any kind of signal dependent classification. The additional pre-processing is preferably activated through a one bit bitstream element, bs_sbr_preprocessing. When bs_sbr_preprocessing is set to one, the additional processing is enabled. When bs_sbr_preprocessing is set to zero, the additional pre-processing is disabled. The additional processing preferable utilizes a preGain curve that is used by the high frequency generator to scale the lowband, $X_{Low}$, for each patch. For example, the preGain curve may be calculated according to:

$$\text{preGain}(k) = 10^{(meanNrg - lowEnvSlope(k))/20}, 0 \le k < k_0$$

where $k_0$ is the first QMF subband in the master frequency band table and lowEnvSlope is calculated using a function that computes coefficients of a best fitting polynomial (in a least-squares sense), such as polyfit ( ) For example, $$\text{polyfit}(3, k_0, x\_lowband, lowEnv, lowEnvSlope);$$

may be employed (using a third degree polynomial) and where $$lowEnv(k) = 10 \log_{10} \frac{\varphi_k(0, 0)}{numTimeSlots \cdot RATE + 6}, 0 \le k < k_0$$

where x_lowband (k)=[0 . . . $k_0$−1], numTimeSlot is the number of SBR envelope time slots that exist within a frame, RATE is a constant indicating the number of QMF subband samples per timeslot (e.g., 2), $\varphi_k$ is a linear prediction filter coefficient (potentially obtained from the covariance method) and where $$meanNrg = \frac{\sum_{k=0}^{k_0-1} lowEnv(k)}{k_0}.$$

A bitstream generated in accordance with the MPEG USAC standard (sometimes referred to herein as a "USAC bitstream") includes encoded audio content and typically includes metadata indicative of each type of spectral band replication processing to be applied by a decoder to decode audio content of the USAC bitstream, and/or metadata which controls such spectral band replication processing and/or is indicative of at least one characteristic or parameter of at least one SBR tool and/or eSBR tool to be employed to decode audio content of the USAC bitstream.

Herein, we use the expression "enhanced SBR metadata" (or "eSBR metadata") to denote metadata indicative of each type of spectral band replication processing to be applied by a decoder to decode audio content of an encoded audio bitstream (e.g., a USAC bitstream) and/or which controls such spectral band replication processing, and/or is indicative of at least one characteristic or parameter of at least one SBR tool and/or eSBR tool to be employed to decode such audio content, but which is not described or mentioned in the MPEG-4 AAC standard. An example of eSBR metadata is the metadata (indicative of, or for controlling, spectral band replication processing) which is described or mentioned in the MPEG USAC standard but not in the MPEG-4 AAC standard. Thus, eSBR metadata herein denotes metadata which is not SBR metadata, and SBR metadata herein denotes metadata which is not eSBR metadata.

A USAC bitstream may include both SBR metadata and eSBR metadata. More specifically, a USAC bitstream may include eSBR metadata which controls the performance of eSBR processing by a decoder, and SBR metadata which controls the performance of SBR processing by the decoder. In accordance with typical embodiments of the present invention, eSBR metadata (e.g., eSBR-specific configuration data) is included (in accordance with the present invention) in an MPEG-4 AAC bitstream (e.g., in the sbr_extension ( ) container at the end of an SBR payload).

Performance of eSBR processing, during decoding of an encoded bitstream using an eSBR tool set (comprising at least one eSBR tool), by a decoder regenerates the high frequency band of the audio signal, based on replication of sequences of harmonics which were truncated during encoding. Such eSBR processing typically adjusts the spectral envelope of the generated high frequency band and applies inverse filtering, and adds noise and sinusoidal components in order to recreate the spectral characteristics of the original audio signal.

In accordance with typical embodiments of the invention, eSBR metadata is included (e.g., a small number of control bits which are eSBR metadata are included) in one or more of metadata segments of an encoded audio bitstream (e.g., an MPEG-4 AAC bitstream) which also includes encoded audio data in other segments (audio data segments). Typically, at least one such metadata segment of each block of the bitstream is (or includes) a fill element (including an identifier indicating the start of the fill element), and the eSBR metadata is included in the fill element after the identifier. FIG. 1 is a block diagram of an exemplary audio processing chain (an audio data processing system), in which one or more of the elements of the system may be configured in accordance with an embodiment of the present invention. The system includes the following elements, coupled together as shown: encoder 1, delivery subsystem 2, decoder 3, and post-processing unit 4. In variations on the system shown, one or more of the elements are omitted, or additional audio data processing units are included.

In some implementations, encoder 1 (which optionally includes a pre-processing unit) is configured to accept PCM (time-domain) samples comprising audio content as input, and to output an encoded audio bitstream (having format which is compliant with the MPEG-4 AAC standard) which is indicative of the audio content. The data of the bitstream that are indicative of the audio content are sometimes referred to herein as "audio data" or "encoded audio data." If the encoder is configured in accordance with a typical embodiment of the present invention, the audio bitstream output from the encoder includes eSBR metadata (and typically also other metadata) as well as audio data.

One or more encoded audio bitstreams output from encoder 1 may be asserted to encoded audio delivery subsystem 2. Subsystem 2 is configured to store and/or deliver each encoded bitstream output from encoder 1. An encoded audio bitstream output from encoder 1 may be stored by subsystem 2 (e.g., in the form of a DVD or Blu ray disc), or transmitted by subsystem 2 (which may implement a transmission link or network), or may be both stored and transmitted by subsystem 2.

Decoder 3 is configured to decode an encoded MPEG-4 AAC audio bitstream (generated by encoder 1) which it receives via subsystem 2. In some embodiments, decoder 3 is configured to extract eSBR metadata from each block of the bitstream, and to decode the bitstream (including by performing eSBR processing using the extracted eSBR metadata) to generate decoded audio data (e.g., streams of decoded PCM audio samples). In some embodiments, decoder 3 is configured to extract SBR metadata from the bitstream (but to ignore eSBR metadata included in the bitstream), and to decode the bitstream (including by performing SBR processing using the extracted SBR metadata) to generate decoded audio data (e.g., streams of decoded PCM audio samples). Typically, decoder 3 includes a buffer which stores (e.g., in a non-transitory manner) segments of the encoded audio bitstream received from subsystem 2.

Post-processing unit 4 of FIG. 1 is configured to accept a stream of decoded audio data from decoder 3 (e.g., decoded PCM audio samples), and to perform post processing thereon. Post-processing unit may also be configured to render the post-processed audio content (or the decoded audio received from decoder 3) for playback by one or more speakers.

Figure 2:
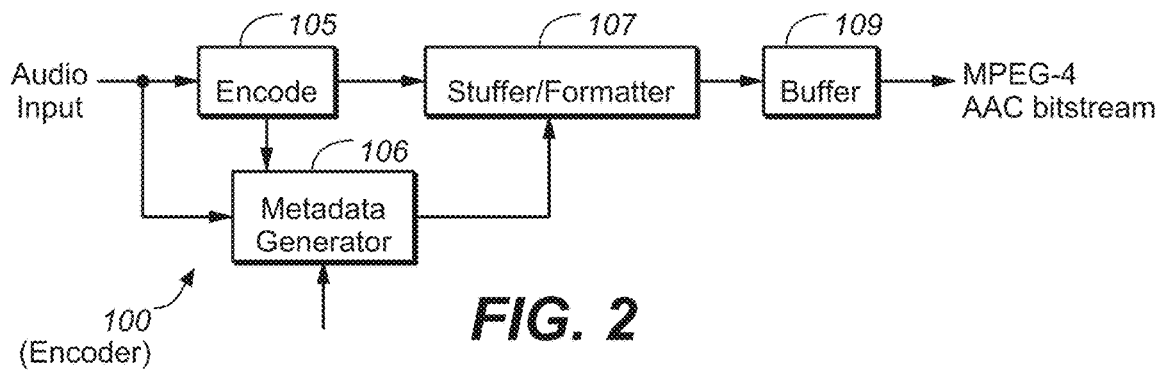
FIG. 2 is a block diagram of an encoder which is an embodiment of the inventive audio processing unit.

FIG. 2 is a block diagram of an encoder (100) which is an embodiment of the inventive audio processing unit. Any of the components or elements of encoder 100 may be implemented as one or more processes and/or one or more circuits (e.g., ASICs, FPGAs, or other integrated circuits), in hardware, software, or a combination of hardware and software. Encoder 100 includes encoder 105, stuffer/formatter stage 107, metadata generation stage 106, and buffer memory 109, connected as shown. Typically also, encoder 100 includes other processing elements (not shown). Encoder 100 is configured to convert an input audio bitstream to an encoded output MPEG-4 AAC bitstream.

Metadata generator 106 is coupled and configured to generate (and/or pass through to stage 107) metadata (including eSBR metadata and SBR metadata) to be included by stage 107 in the encoded bitstream to be output from encoder 100.

Encoder 105 is coupled and configured to encode (e.g., by performing compression thereon) the input audio data, and to assert the resulting encoded audio to stage 107 for inclusion in the encoded bitstream to be output from stage 107.

Stage 107 is configured to multiplex the encoded audio from encoder 105 and the metadata (including eSBR metadata and SBR metadata) from generator 106 to generate the encoded bitstream to be output from stage 107, preferably so that the encoded bitstream has format as specified by one of the embodiments of the present invention.

Buffer memory 109 is configured to store (e.g., in a non-transitory manner) at least one block of the encoded audio bitstream output from stage 107, and a sequence of the blocks of the encoded audio bitstream is then asserted from buffer memory 109 as output from encoder 100 to a delivery system.

Figure 3:
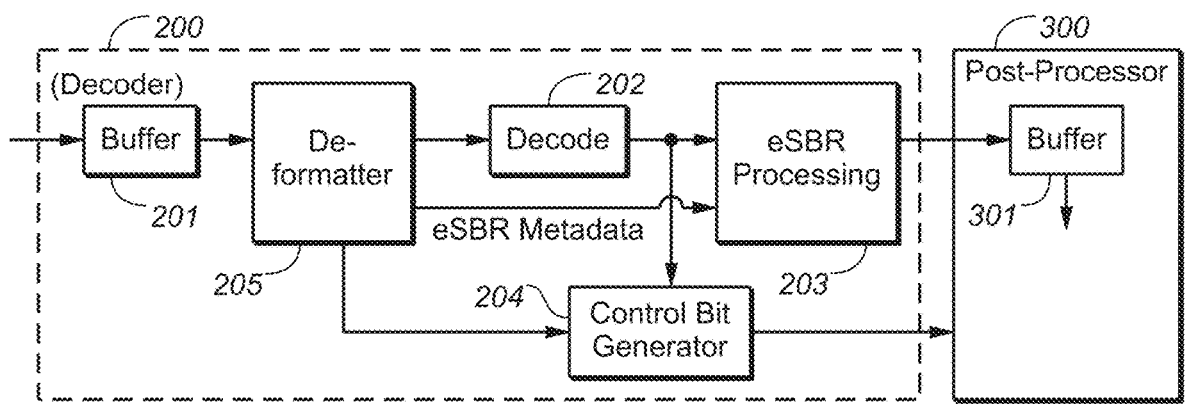
FIG. 3 is a block diagram of a system including a decoder which is an embodiment of the inventive audio processing unit, and optionally also a post-processor coupled thereto.

FIG. 3 is a block diagram of a system including decoder (200) which is an embodiment of the inventive audio processing unit, and optionally also a post-processor (300) coupled thereto. Any of the components or elements of decoder 200 and post-processor 300 may be implemented as one or more processes and/or one or more circuits (e.g., ASICs, FPGAs, or other integrated circuits), in hardware, software, or a combination of hardware and software. Decoder 200 comprises buffer memory 201, bitstream payload deformatter (parser) 205, audio decoding subsystem 202 (sometimes referred to as a "core" decoding stage or "core" decoding subsystem), cSBR processing stage 203, and control bit generation stage 204, connected as shown. Typically also, decoder 200 includes other processing elements (not shown).

Buffer memory (buffer) 201 stores (e.g., in a non-transitory manner) at least one block of an encoded MPEG-4 AAC audio bitstream received by decoder 200. In operation of decoder 200, a sequence of the blocks of the bitstream is asserted from buffer 201 to deformatter 205.

Figure 4:
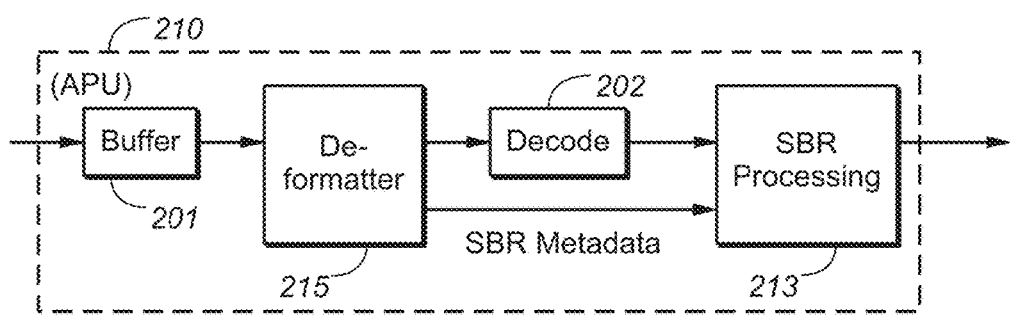
FIG. 4 is a block diagram of a decoder which is an embodiment of the inventive audio processing unit.
Figure 6:
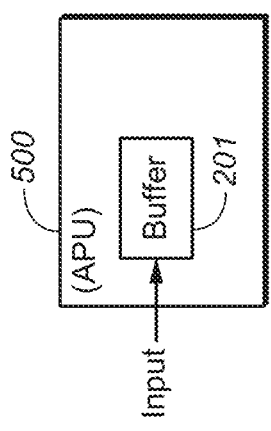
FIG. 6 is a block diagram of another embodiment of the inventive audio processing unit.

In variations on the FIG. 3 embodiment (or the FIG. 4 embodiment to be described), an APU which is not a decoder (e.g., APU 500 of FIG. 6) includes a buffer memory (e.g., a buffer memory identical to buffer 201) which stores (e.g., in a non-transitory manner) at least one block of an encoded audio bitstream (e.g., an MPEG-4 AAC audio bitstream) of the same type received by buffer 201 of FIG. 3 or FIG. 4 (i.e., an encoded audio bitstream which includes eSBR metadata).

With reference again to FIG. 3, deformatter 205 is coupled and configured to demultiplex each block of the bitstream to extract SBR metadata (including quantized envelope data) and eSBR metadata (and typically also other metadata) therefrom, to assert at least the eSBR metadata and the SBR metadata to eSBR processing stage 203, and typically also to assert other extracted metadata to decoding subsystem 202 (and optionally also to control bit generator 204). Deformatter 205 is also coupled and configured to extract audio data from each block of the bitstream, and to assert the extracted audio data to decoding subsystem (decoding stage) 202.

The system of FIG. 3 optionally also includes post-processor 300. Post-processor 300 includes buffer memory (buffer) 301 and other processing elements (not shown) including at least one processing element coupled to buffer 301. Buffer 301 stores (e.g., in a non-transitory manner) at least one block (or frame) of the decoded audio data received by post-processor 300 from decoder 200. Processing elements of post-processor 300 are coupled and configured to receive and adaptively process a sequence of the blocks (or frames) of the decoded audio output from buffer 301, using metadata output from decoding subsystem 202 (and/or deformatter 205) and/or control bits output from stage 204 of decoder 200.

Audio decoding subsystem 202 of decoder 200 is configured to decode the audio data extracted by parser 205 (such decoding may be referred to as a "core" decoding operation) to generate decoded audio data, and to assert the decoded audio data to eSBR processing stage 203. The decoding is performed in the frequency domain and typically includes inverse quantization followed by spectral processing. Typically, a final stage of processing in subsystem 202 applies a frequency domain-to-time domain transform to the decoded frequency domain audio data, so that the output of subsystem is time domain, decoded audio data. Stage 203 is configured to apply SBR tools and eSBR tools indicated by the eSBR metadata and the eSBR (extracted by parser 205) to the decoded audio data (i.e., to perform SBR and eSBR processing on the output of decoding subsystem 202 using the SBR and eSBR metadata) to generate the fully decoded audio data which is output (e.g., to post-processor 300) from decoder 200. Typically, decoder 200 includes a memory (accessible by subsystem 202 and stage 203) which stores the deformatted audio data and metadata output from deformatter 205, and stage 203 is configured to access the audio data and metadata (including SBR metadata and cSBR metadata) as needed during SBR and eSBR processing. The SBR processing and cSBR processing in stage 203 may be considered to be post-processing on the output of core decoding subsystem 202. Optionally, decoder 200 also includes a final upmixing subsystem (which may apply parametric stereo ("PS") tools defined in the MPEG-4 AAC standard, using PS metadata extracted by deformatter 205 and/or control bits generated in subsystem 204) which is coupled and configured to perform upmixing on the output of stage 203 to generated fully decoded, upmixed audio which is output from decoder 200. Alternatively, post-processor 300 is configured to perform upmixing on the output of decoder 200 (e.g., using PS metadata extracted by deformatter 205 and/or control bits generated in subsystem 204).

In response to metadata extracted by deformatter 205, control bit generator 204 may generate control data, and the control data may be used within decoder 200 (e.g., in a final upmixing subsystem) and/or asserted as output of decoder 200 (e.g., to post-processor 300 for use in post-processing). In response to metadata extracted from the input bitstream (and optionally also in response to control data), stage 204 may generate (and assert to post-processor 300) control bits indicating that decoded audio data output from cSBR processing stage 203 should undergo a specific type of post-processing. In some implementations, decoder 200 is configured to assert metadata extracted by deformatter 205 from the input bitstream to post-processor 300, and post-processor 300 is configured to perform post-processing on the decoded audio data output from decoder 200 using the metadata.

FIG. 4 is a block diagram of an audio processing unit ("APU") (210) which is another embodiment of the inventive audio processing unit. APU 210 is a legacy decoder which is not configured to perform cSBR processing. Any of the components or elements of APU 210 may be implemented as one or more processes and/or one or more circuits (e.g., ASICs, FPGAs, or other integrated circuits), in hardware, software, or a combination of hardware and software. APU 210 comprises buffer memory 201, bitstream payload deformatter (parser) 215, audio decoding subsystem 202 (sometimes referred to as a "core" decoding stage or "core" decoding subsystem), and SBR processing stage 213, connected as shown. Typically also, APU 210 includes other processing elements (not shown). APU 210 may represent, for example, an audio encoder, decoder or transcoder.

Elements 201 and 202 of APU 210 are identical to the identically numbered elements of decoder 200 (of FIG. 3) and the above description of them will not be repeated. In operation of APU 210, a sequence of blocks of an encoded audio bitstream (an MPEG-4 AAC bitstream) received by APU 210 is asserted from buffer 201 to deformatter 215.

Deformatter 215 is coupled and configured to demultiplex each block of the bitstream to extract SBR metadata (including quantized envelope data) and typically also other metadata therefrom, but to ignore eSBR metadata that may be included in the bitstream in accordance with any embodiment of the present invention. Deformatter 215 is configured to assert at least the SBR metadata to SBR processing stage 213. Deformatter 215 is also coupled and configured to extract audio data from each block of the bitstream, and to assert the extracted audio data to decoding subsystem (decoding stage) 202.

Audio decoding subsystem 202 of decoder 200 is configured to decode the audio data extracted by deformatter 215 (such decoding may be referred to as a "core" decoding operation) to generate decoded audio data, and to assert the decoded audio data to SBR processing stage 213. The decoding is performed in the frequency domain. Typically, a final stage of processing in subsystem 202 applies a frequency domain-to-time domain transform to the decoded frequency domain audio data, so that the output of subsystem is time domain, decoded audio data. Stage 213 is configured to apply SBR tools (but not eSBR tools) indicated by the SBR metadata (extracted by deformatter 215) to the decoded audio data (i.e., to perform SBR processing on the output of decoding subsystem 202 using the SBR metadata) to generate the fully decoded audio data which is output (e.g., to post-processor 300) from APU 210. Typically, APU 210 includes a memory (accessible by subsystem 202 and stage 213) which stores the deformatted audio data and metadata output from deformatter 215, and stage 213 is configured to access the audio data and metadata (including SBR metadata) as needed during SBR processing. The SBR processing in stage 213 may be considered to be post-processing on the output of core decoding subsystem 202. Optionally, APU 210 also includes a final upmixing subsystem (which may apply parametric stereo ("PS") tools defined in the MPEG-4 AAC standard, using PS metadata extracted by deformatter 215) which is coupled and configured to perform upmixing on the output of stage 213 to generated fully decoded, upmixed audio which is output from APU 210. Alternatively, a post-processor is configured to perform upmixing on the output of APU 210 (e.g., using PS metadata extracted by deformatter 215 and/or control bits generated in APU 210).

Various implementations of encoder 100, decoder 200, and APU 210 are configured to perform different embodiments of the inventive method.

In accordance with some embodiments, eSBR metadata is included (e.g., a small number of control bits which are eSBR metadata are included) in an encoded audio bitstream (e.g., an MPEG-4 AAC bitstream), such that legacy decoders (which are not configured to parse the eSBR metadata, or to use any eSBR tool to which the eSBR metadata pertains) can ignore the eSBR metadata but nevertheless decode the bitstream to the extent possible without use of the eSBR metadata or any eSBR tool to which the eSBR metadata pertains, typically without any significant penalty in decoded audio quality. However, eSBR decoders configured to parse the bitstream to identify the eSBR metadata and to use at least one eSBR tool in response to the eSBR metadata, will enjoy the benefits of using at least one such eSBR tool. Therefore, embodiments of the invention provide a means for efficiently transmitting enhanced spectral band replication (eSBR) control data or metadata in a backward-compatible fashion.

Typically, the eSBR metadata in the bitstream is indicative of (e.g., is indicative of at least one characteristic or parameter of) one or more of the following eSBR tools (which are described in the MPEG USAC standard, and which may or may not have been applied by an encoder during generation of the bitstream):

Harmonic transposition; and

QMF-patching additional pre-processing (pre-flattening).

For example, the eSBR metadata included in the bitstream may be indicative of values of the parameters (described in the MPEG USAC standard and in the present disclosure): sbrPatchingMode [ch], sbrOversamplingFlag [ch], sbrPitchInBins [ch], sbrPitchInBins [ch], and bs_sbr_pre-processing.

Herein, the notation X[ch], where X is some parameter, denotes that the parameter pertains to channel ("ch") of audio content of an encoded bitstream to be decoded. For simplicity, we sometimes omit the expression [ch], and assume the relevant parameter pertains to a channel of audio content.

Herein, the notation X[ch] [env], where X is some parameter, denotes that the parameter pertains to SBR envelope ("env") of channel ("ch") of audio content of an encoded bitstream to be decoded. For simplicity, we sometimes omit the expressions [env] and [ch], and assume the relevant parameter pertains to an SBR envelope of a channel of audio content.

During decoding of an encoded bitstream, performance of harmonic transposition during an eSBR processing stage of the decoding (for each channel, "ch", of audio content indicated by the bitstream) is controlled by the following eSBR metadata parameters: sbrPatchingMode [ch]: sbrOversamplingFlag [ch]; sbrPitchInBinsFlag [ch]; and sbrPitchInBins [ch].

The value "sbrPatchingMode [ch]" indicates the transposer type used in eSBR: sbrPatchingMode [ch]=1 indicates linear transposition patching as described in Section 4.6.18 of the MPEG-4 AAC standard (as used with either high-quality SBR or low-power SBR); sbrPatchingMode [ch]=0 indicates harmonic SBR patching as described in Section 7.5.3 or 7.5.4 of the MPEG USAC standard.

The value "sbrOversamplingFlag [ch]" indicates the use of signal adaptive frequency domain oversampling in eSBR in combination with the DFT based harmonic SBR patching as described in Section 7.5.3 of the MPEG USAC standard. This flag controls the size of the DFTs that are utilized in the transposer: 1 indicates signal adaptive frequency domain oversampling enabled as described in Section 7.5.3.1 of the MPEG USAC standard; 0 indicates signal adaptive frequency domain oversampling disabled as described in Section 7.5.3.1 of the MPEG USAC standard.

The value "sbrPitchInBinsFlag [ch]" controls the interpretation of the sbrPitchInBins [ch] parameter: 1 indicates that the value in sbrPitchInBins [ch] is valid and greater than zero; 0 indicates that the value of sbrPitchInBins [ch] is set to zero.

The value "sbrPitchInBins [ch]" controls the addition of cross product terms in the SBR harmonic transposer. The value sbrPitchinBins [ch] is an integer value in the range [0,127] and represents the distance measured in frequency bins for a 1536-line DFT acting on the sampling frequency of the core coder.

In the case that an MPEG-4 AAC bitstream is indicative of an SBR channel pair whose channels are not coupled (rather than a single SBR channel), the bitstream is indicative of two instances of the above syntax (for harmonic or non-harmonic transposition), one for each channel of the sbr_channel_pair_element ( ).

The harmonic transposition of the eSBR tool typically improves the quality of decoded musical signals at relatively low cross over frequencies. Non-harmonic transposition (that is, legacy spectral patching) typically improves speech signals. Hence, a starting point in the decision as to which type of transposition is preferable for encoding specific audio content is to select the transposition method depending on speech/music detection with harmonic transposition be employed on the musical content and spectral patching on the speed content.

Performance of pre-flattening during eSBR processing is controlled by the value of a one-bit eSBR metadata parameter known as "bs_sbr_preprocessing", in the sense that pre-flattening is either performed or not performed depending on the value of this single bit. When the SBR QMF-patching algorithm, as described in Section 4.6.18.6.3 of the MPEG-4 AAC standard, is used, the step of pre-flattening may be performed (when indicated by the "bs_sbr_preprocessing" parameter) in an effort to avoid discontinuities in the shape of the spectral envelope of a high frequency signal being input to a subsequent envelope adjuster (the envelope adjuster performs another stage of the eSBR processing). The pre-flattening typically improves the operation of the subsequent envelope adjustment stage, resulting in a high-band signal that is perceived to be more stable.

The overall bitrate requirement for including in an MPEG-4 AAC bitstream eSBR metadata indicative of the above-mentioned eSBR tools (harmonic transposition and pre-flattening) is expected to be on the order of a few hundreds of bits per second because only the differential control data needed to perform eSBR processing is transmitted in accordance with some embodiments of the invention. Legacy decoders can ignore this information because it is included in a backward compatible manner (as will be explained later). Therefore, the detrimental effect on bitrate associated with of inclusion of eSBR metadata is negligible, for a number of reasons, including the following:

The bitrate penalty (due to including the eSBR metadata) is a very small fraction of the total bitrate because only the differential control data needed to perform eSBR processing is transmitted (and not a simulcast of the SBR control data); and The tuning of SBR related control information does not typically depend of the details of the transposition.

Examples of when the control data does depend on the operation of the transposer are discussed later in this application.

Thus, embodiments of the invention provide a means for efficiently transmitting enhanced spectral band replication (eSBR) control data or metadata in a backward-compatible fashion. This efficient transmission of the eSBR control data reduces memory requirements in decoders, encoders, and transcoders employing aspects of the invention, while having no tangible adverse effect on bitrate. Moreover, the complexity and processing requirements associated with performing eSBR in accordance with embodiments of the invention are also reduced because the SBR data needs to be processed only once and not simulcast, which would be the case if eSBR was treated as a completely separate object type in MPEG-4 AAC instead of being integrated into the MPEG-4 AAC codec in a backward-compatible manner.

Figure 7:
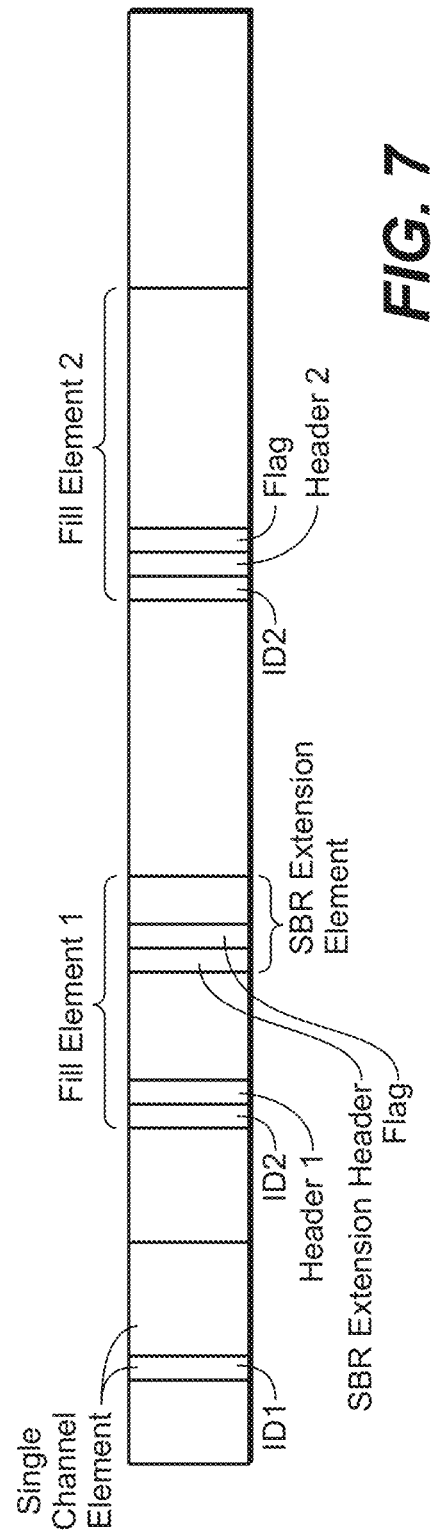
FIG. 7 is a diagram of a block of an MPEG-4 AAC bitstream, including segments into which it is divided.

Next, with reference to FIG. 7, we describe elements of a block ("raw_data_block") of an MPEG-4 AAC bitstream in which eSBR metadata is included in accordance with some embodiments of the present invention. FIG. 7 is a diagram of a block (a "raw_data_block") of the MPEG-4 AAC bitstream, showing some of the segments thereof.

A block of an MPEG-4 AAC bitstream may include at least one "single_channel_element ( )" (e.g., the single channel element shown in FIG. 7), and/or at least one "channel_pair_element ( ) (not specifically shown in FIG. 7 although it may be present), including audio data for an audio program. The block may also include a number of "fill_elements" (e.g., fill element 1 and/or fill element 2 of FIG. 7) including data (e.g., metadata) related to the program. Each "single_channel_element ( ) includes an identifier (e.g., "ID1" of FIG. 7) indicating the start of a single channel element, and can include audio data indicative of a different channel of a multi-channel audio program. Each "channel pair_element includes an identifier (not shown in FIG. 7) indicating the start of a channel pair element, and can include audio data indicative of two channels of the program.

A fill_element (referred to herein as a fill element) of an MPEG-4 AAC bitstream includes an identifier ("ID2" of FIG. 7) indicating the start of a fill element, and fill data after the identifier. The identifier ID2 may consist of a three bit unsigned integer transmitted most significant bit first ("uimsbf") having a value of 0×6. The fill data can include an extension_payload ( ) element (sometimes referred to herein as an extension payload) whose syntax is shown in Table 4.57 of the MPEG-4 AAC standard. Several types of extension payloads exist and are identified through the "extension_type" parameter, which is a four bit unsigned integer transmitted most significant bit first ("uimsbf").

The fill data (e.g., an extension payload thereof) can include a header or identifier (e.g., "header1" of FIG. 7) which indicates a segment of fill data which is indicative of an SBR object (i.e., the header initializes an "SBR object" type, referred to as sbr_extension_data ( ) in the MPEG-4 AAC standard). For example, a spectral band replication (SBR) extension payload is identified with the value of '1101' or '1110' for the extension_type field in the header, with the identifier '1101' identifying an extension payload with SBR data and '1110' identifying and extension payload with SBR data with a Cyclic Redundancy Check (CRC) to verify the correctness of the SBR data . . .

When the header (e.g., the extension_type field) initializes an SBR object type, SBR metadata (sometimes referred to herein as "spectral band replication data," and referred to as sbr_data ( ) in the MPEG-4 AAC standard) follows the header, and at least one spectral band replication extension element (e.g., the "SBR extension element" of fill element 1 of FIG. 7) can follow the SBR metadata. Such a spectral band replication extension element (a segment of the bitstream) is referred to as an "sbr_extension ( )" container in the MPEG-4 AAC standard. A spectral band replication extension element optionally includes a header (e.g., "SBR extension header" of fill element 1 of FIG. 7).

The MPEG-4 AAC standard contemplates that a spectral band replication extension element can include PS (parametric stereo) data for audio data of a program. The MPEG-4 AAC standard contemplates that when the header of a fill element (e.g., of an extension payload thereof) initializes an SBR object type (as does "header1" of FIG. 7) and a spectral band replication extension element of the fill element includes PS data, the fill element (e.g., the extension payload thereof) includes spectral band replication data, and a "bs_extension_id" parameter whose value (i.e., bs_extension_id=2) indicates that PS data is included in a spectral band replication extension element of the fill element.

In accordance with some embodiments of the present invention, eSBR metadata (e.g., a flag indicative of whether enhanced spectral band replication (cSBR) processing is to be performed on audio content of the block) is included in a spectral band replication extension element of a fill element. For example, such a flag is indicated in fill element 1 of FIG. 7, where the flag occurs after the header (the "SBR extension header" of fill element 1) of "SBR extension element" of fill element 1. Optionally, such a flag and additional eSBR metadata are included in a spectral band replication extension element after the spectral band replication extension element's header (e.g., in the SBR extension element of fill element 1 in FIG. 7, after the SBR extension header). In accordance with some embodiments of the present invention, a fill element which includes eSBR metadata also includes a "bs_extension_id" parameter whose value (e.g., bs_extension_id=3) indicates that eSBR metadata is included in the fill element and that eSBR processing is to be performed on audio content of the relevant block.

In accordance with some embodiments of the invention, eSBR metadata is included in a fill element (e.g., fill element 2 of FIG. 7) of an MPEG-4 AAC bitstream other than in a spectral band replication extension element (SBR extension element) of the fill element. This is because fill elements containing an extension_payload ( ) with SBR data or SBR data with a CRC do not contain any other extension payload of any other extension type. Therefore, in embodiments where eSBR metadata is stored its own extension payload, a separate fill element is used to store the eSBR metadata. Such a fill element includes an identifier (e.g., "ID2" of FIG. 7) indicating the start of a fill element, and fill data after the identifier. The fill data can include an extension_payload ( ) element (sometimes referred to herein as an extension payload) whose syntax is shown in Table 4.57 of the MPEG-4 AAC standard. The fill data (e.g., an extension payload thereof) includes a header (e.g., "header2" of fill element 2 of FIG. 7) which is indicative of an eSBR object (i.e., the header initializes an enhanced spectral band replication (cSBR) object type), and the fill data (e.g., an extension payload thereof) includes eSBR metadata after the header. For example, fill element 2 of FIG. 7 includes such a header ("header2") and also includes, after the header, eSBR metadata (i.e., the "flag" in fill element 2, which is indicative of whether enhanced spectral band replication (eSBR) processing is to be performed on audio content of the block). Optionally, additional eSBR metadata is also included in the fill data of fill element 2 of FIG. 7, after header2. In the embodiments being described in the present paragraph, the header (e.g., header2 of FIG. 7) has an identification value which is not one of the conventional values specified in Table 4.57 of the MPEG-4 AAC standard, and is instead indicative of an eSBR extension payload (so that the header's extension_type field indicates that the fill data includes eSBR metadata).

In a first class of embodiments, the invention is an audio processing unit (e.g., a decoder), comprising:

a memory (e.g., buffer 201 of FIG. 3 or 4) configured to store at least one block of an encoded audio bitstream (e.g., at least one block of an MPEG-4 AAC bitstream);

a bitstream payload deformatter (e.g., element 205 of FIG. 3 or element 215 of FIG. 4) coupled to the memory and configured to demultiplex at least one portion of said block of the bitstream; and a decoding subsystem (e.g., elements 202 and 203 of FIG. 3, or elements 202 and 213 of FIG. 4), coupled and configured to decode at least one portion of audio content of said block of the bitstream, wherein the block includes:

a fill element, including an identifier indicating a start of the fill element (e.g., the "id_syn_ele" identifier having value 0×6, of Table 4.85 of the MPEG-4 AAC standard), and fill data after the identifier, wherein the fill data includes:

at least one flag identifying whether enhanced spectral band replication (eSBR) processing is to be performed on audio content of the block (e.g., using spectral band replication data and eSBR metadata included in the block).

The flag is eSBR metadata, and an example of the flag is the sbrPatchingMode flag. Another example of the flag is the harmonicSBR flag. Both of these flags indicate whether a base form of spectral band replication or an enhanced form of spectral replication is to be performed on the audio data of the block. The base form of spectral replication is spectral patching, and the enhanced form of spectral band replication is harmonic transposition.

In some embodiments, the fill data also includes additional eSBR metadata (i.e., eSBR metadata other than the flag).

The memory may be a buffer memory (e.g., an implementation of buffer 201 of FIG. 4) which stores (e.g., in a non-transitory manner) the at least one block of the encoded audio bitstream.

It is estimated that the complexity of performance of eSBR processing (using the eSBR harmonic transposition and pre-flattening) by an eSBR decoder during decoding of an MPEG-4 AAC bitstream which includes eSBR metadata (indicative of these eSBR tools) would be as follows (for typical decoding with the indicated parameters):

Harmonic transposition (16 kbps, 14400/28800 Hz)
DFT based: 3.68 WMOPS (weighted million operations per second);
QMF based: 0.98 WMOPS;
QMF-patching pre-processing (pre-flattening): 0.1 WMOPS.

It is known that DFT based transposition typically performs better than the QMF based transposition for transients.

In accordance with some embodiments of the present invention, a fill element (of an encoded audio bitstream) which includes eSBR metadata also includes a parameter (e.g., a "bs extension_id" parameter) whose value (e.g., bs_extension_id=3) signals that eSBR metadata is included in the fill element and that eSBR processing is to be performed on audio content of the relevant block, and/or or a parameter (e.g., the same "bs_extension_id" parameter) whose value (e.g., bs_extension_id=2) signals that an sbr_extension ( ) container of the fill element includes PS data. For example, as indicated in Table 1 below, such a parameter having the value bs_extension_id=2 may signal that an sbr_extension ( ) container of the fill element includes PS data, and such a parameter having the value bs_extension_id=3 may signal that an sbr_extension ( ) container of the fill element includes eSBR metadata:

TABLE 1

| bs_extension_id | Meaning |
| --- | --- |
| 0 | Reserved |
| 1 | Reserved |
| 2 | EXTENSION_ID_PS |
| 3 | EXTENSION_ID_ESBR |

In accordance with some embodiments of the invention, the syntax of each spectral band replication extension element which includes eSBR metadata and/or PS data is as indicated in Table 2 below (in which "sbr_extension ( )" denotes a container which is the spectral band replication extension element, "bs_extension_id" is as described in Table 1 above, "ps_data" denotes PS data, and "esbr_data" denotes eSBR metadata):

TABLE 2

```
sbr_extension(bs_extension_id, num_bits_left)
{
    switch (bs_extension_id) {
    case EXTENSION_ID_PS:
        num_bits_left -= ps_data( );                  Note 1
        break;
    case EXTENSION_ID_ESBR:
        num_bits_left -= esbr_data();                 Note 2
        break;
    default:
        bs_fill_bits;
        num_bits_left = 0;
        break;
    }
}
```

Note 1:
ps_data( ) returns the number of bits read.
Note 2:
esbr_data( ) returns the number of bits read.

In an exemplary embodiment, the esbr_data ( ) referred to in Table 2 above is indicative of values of the following metadata parameters:
1. the one-bit metadata parameter, "bs_sbr_preprocessing"; and
2. for each channel ("ch") of audio content of the encoded bitstream to be decoded, each of the above-described parameters: "sbrPatchingMode [ch]"; "sbrOversamplingFlag [ch]"; "sbrPitchInBinsFlag [ch]"; and "sbrPitchInBins [ch]".

For example, in some embodiments, the esbr_data ( ) may have the syntax indicated in Table 3. to indicate these metadata parameters:

TABLE 3

| Syntax | No. of bits |
| --- | --- |
| esbr_data(id_aac, bs_coupling) | |
| { | |

TABLE 3-continued

| Syntax | No. of bits |
| --- | --- |
| bs_sbr_preprocessing; | 1 |
| if (id_aac == ID_SCE) { | |
|   if (sbrPatchingMode[0] == 0) { | 1 |
|     sbrOversamplingFlag[0]; | 1 |
|     if (sbrPitchInBinsFlag[0]) | 1 |
|       sbrPitchInBins[0]; | 7 |
|     else | |
|       sbrPitchInBins[0] = 0; | |
|   } else { | |
|     sbrOversamplingFlag[0] = 0; | |
|     sbrPitchInBins[0] = 0; | |
|   } | |
| } else if (id_aac == ID_CPE) { | |
|   If (bs_coupling) { | |
|     if (sbrPatchingMode[0,1] == 0) { | 1 |
|       sbrOversamplingFlag[0,1]; | 1 |
|       if (sbrPitchInBinsFlag[0,1]) | 1 |
|         sbrPitchInBins[0,1]; | 7 |
|       else | |
|         sbrPitchInBins[0,1] = 0; | |
|     } else { | |
|       sbrOversamplingFlag[0,1] = 0; | |
|       sbrPitchInBins[0,1] = 0; | |
|     } | |
|   } else {   /* bs_coupling == 0 */ | |
|     if (sbrPatchingMode[0] == 0) { | 1 |
|       sbrOversamplingFlag[0]; | 1 |
|       if (sbrPitchInBinsFlag[0]) | 1 |
|         sbrPitchInBins[0]; | 7 |
|       else | |
|         sbrPitchInBins[0] = 0; | |
|     } else { | |
|       sbrOversamplingFlag[0] = 0; | |
|       sbrPitchInBins[0] = 0; | |
|     } | |
|     if (sbrPatchingMode[1] == 0) { | 1 |
|       sbrOversamplingFlag[1]; | 1 |
|       if (sbrPitchInBinsFlag[1]) | 1 |
|         sbrPitchInBins[1]; | 7 |
|       else | |
|         sbrPitchInBins[1] = 0; | |
|     } else { | |
|       sbrOversamplingFlag[1] = 0; | |
|       sbrPitchInBins[1] = 0; | |
|     } | |
|   } | |
| } | |
| } | |

Note:
bs_sbr_preprocessing is defined as described in section 6.2.12 of ISO/IEC 23003-3:2012. sbrPatchingMode[ch], sbrOversamplingFlag[ch], sbrPitchInBinsFlag[ch] and sbrPitchInBins[ch] are defined as described in section 7.5 of ISO/IEC 23003-3:2012.

The above syntax enables an efficient implementation of an enhanced form of spectral band replication, such as harmonic transposition, as an extension to a legacy decoder. Specifically, the eSBR data of Table 3 includes only those parameters needed to perform the enhanced form of spectral band replication that are not either already supported in the bitstream or directly derivable from parameters already supported in the bitstream. All other parameters and processing data needed to perform the enhanced form of spectral band replication are extracted from pre-existing parameters in already-defined locations in the bitstream.

For example, an MPEG-4 HE-AAC or HE-AAC v2 compliant decoder may be extended to include an enhanced form of spectral band replication, such as harmonic transposition. This enhanced form of spectral band replication is in addition to the base form of spectral band replication already supported by the decoder. In the context of an MPEG-4 HE-AAC or HE-AAC v2 compliant decoder, this base form of spectral band replication is the QMF spectral patching SBR tool as defined in Section 4.6.18 of the MPEG-4 AAC Standard.

When performing the enhanced form of spectral band replication, an extended HE-AAC decoder may reuse many of the bitstream parameters already included in the SBR extension payload of the bitstream. The specific parameters that may be reused include, for example, the various parameters that determine the master frequency band table. These parameters include bs_start_freq (parameter that determines the start of master frequency table parameter), bs_stop_freq (parameter that determines the stop of master frequency table), bs_freq_scale (parameter that determines the number of frequency bands per octave), and bs_alter_scale (parameter that alters the scale of the frequency bands). The parameters that may be reused also include parameters that determine the noise band table (bs_noise_bands) and the limiter band table parameters (bs_limiter_bands). Accordingly, in various embodiments, at least some of the equivalent parameters specified in the USAC standard are omitted from the bitstream, thereby reducing control overhead in the bitstream. Typically, where a parameter specified in the AAC standard has an equivalent parameter specified in the USAC standard, the equivalent parameter specified in the USAC standard has the same name as the parameter specified in the AAC standard, e.g. the envelope scalefactor EOrigMapped. However, the equivalent parameter specified in the USAC standard typically has a different value, which is "tuned" for the enhanced SBR processing defined in the USAC standard rather than for the SBR processing defined in the AAC standard.

In order to improve the subjective quality for audio content with harmonic frequency structure and strong tonal characteristics, in particular at low bitrates, activation of enhanced SBR is recommended. The values of the corresponding bitstream element (i.e. esbr_data ( ), controlling these tools, may be determined in the encoder by applying a signal dependent classification mechanism. Generally, the usage of the harmonic patching method (sbrPatchingMode==1) is preferable for coding music signals at very low bitrates, where the core codec may be considerably limited in audio bandwidth. This is especially true if these signals include a pronounced harmonic structure. Contrarily, the usage of the regular SBR patching method is preferred for speech and mixed signals, since it provides a better preservation of the temporal structure in speech.

In order to improve the performance of the harmonic transposer, a pre-processing step can be activated (bs_sbr_preprocessing==1) that strives to avoid the introduction of spectral discontinuities of the signal going in to the subsequent envelope adjuster. The operation of the tool is beneficial for signal types where the coarse spectral envelope of the low band signal being used for high frequency reconstruction displays large variations in level.

In order to improve the transient response of the harmonic SBR patching, signal adaptive frequency domain oversampling can be applied (sbrOversamplingFlag==1). Since signal adaptive frequency domain oversampling increases the computational complexity of the transposer, but only brings benefits for frames which contain transients, the use of this tool is controlled by the bitstream element, which is transmitted once per frame and per independent SBR channel.

A decoder operating in the proposed enhanced SBR mode typically needs to be able to switch between legacy and enhanced SBR patching. Therefore, delay may be introduced which can be as long as the duration of one core audio frame, depending on decoder setup. Typically, the delay for both legacy and enhanced SBR patching will be similar.

In addition to the numerous parameters, other data elements may also be reused by an extended HE-AAC decoder when performing an enhanced form of spectral band replication in accordance with embodiments of the invention. For example, the envelope data and noise floor data may also be extracted from the bs_data_env (envelope scalefactors) and bs_noise_env (noise floor scalefactors) data and used during the enhanced form of spectral band replication.

In essence, these embodiments exploit the configuration parameters and envelope data already supported by a legacy HE-AAC or HE-AAC v2 decoder in the SBR extension payload to enable an enhanced form of spectral band replication requiring as little extra transmitted data as possible. The metadata was originally tuned for a base form of HFR (e.g., the spectral translation operation of SBR), but in accordance with embodiments, is used for an enhanced form of HFR (e.g., the harmonic transposition of eSBR). As previously discussed, the metadata generally represents operating parameters (e.g., envelope scale factors, noise floor scale factors, time/frequency grid parameters, sinusoid addition information, variable cross over frequency/band, inverse filtering mode, envelope resolution, smoothing mode, frequency interpolation mode) tuned and intended to be used with the base form of HFR (e.g., linear spectral translation). However, this metadata, combined with additional metadata parameters specific to the enhanced form of HFR (e.g., harmonic transposition), may be used to efficiently and effectively process the audio data using the enhanced form of HFR.

Accordingly, extended decoders that support an enhanced form of spectral band replication may be created in a very efficient manner by relying on already defined bitstream elements (for example, those in the SBR extension payload) and adding only those parameters needed to support the enhanced form of spectral band replication (in a fill element extension payload). This data reduction feature combined with the placement of the newly added parameters in a reserved data field, such as an extension container, substantially reduces the barriers to creating a decoder that supports an enhanced for of spectral band replication by ensuring that the bitstream is backwards-compatible with legacy decoder not supporting the enhanced form of spectral band replication.

In Table 3, the number in the right column indicates the number of bits of the corresponding parameter in the left column.

In some embodiments, the SBR object type defined in MPEG-4 AAC is updated to contain the SBR-Tool and aspects of the enhanced SBR (eSBR) Tool as signaled in the SBR extension element (bs_extension_id==EXTENSION_ID_ESBR). If a decoder detects and supports this SBR extension element, the decoder employs the signaled aspects of the enhanced SBR Tool. The SBR object type updated in this manner is referred to as SBR enhancements.

In some embodiments, the invention is a method including a step of encoding audio data to generate an encoded bitstream (e.g., an MPEG-4 AAC bitstream), including by including eSBR metadata in at least one segment of at least one block of the encoded bitstream and audio data in at least one other segment of the block. In typical embodiments, the method includes a step of multiplexing the audio data with the eSBR metadata in each block of the encoded bitstream. In typical decoding of the encoded bitstream in an eSBR decoder, the decoder extracts the eSBR metadata from the bitstream (including by parsing and demultiplexing the eSBR metadata and the audio data) and uses the eSBR metadata to process the audio data to generate a stream of decoded audio data.

Another aspect of the invention is an eSBR decoder configured to perform eSBR processing (e.g., using at least one of the eSBR tools known as harmonic transposition or pre-flattening) during decoding of an encoded audio bitstream (e.g., an MPEG-4 AAC bitstream) which does not include eSBR metadata. An example of such a decoder will be described with reference to FIG. 5.

Figure 5:
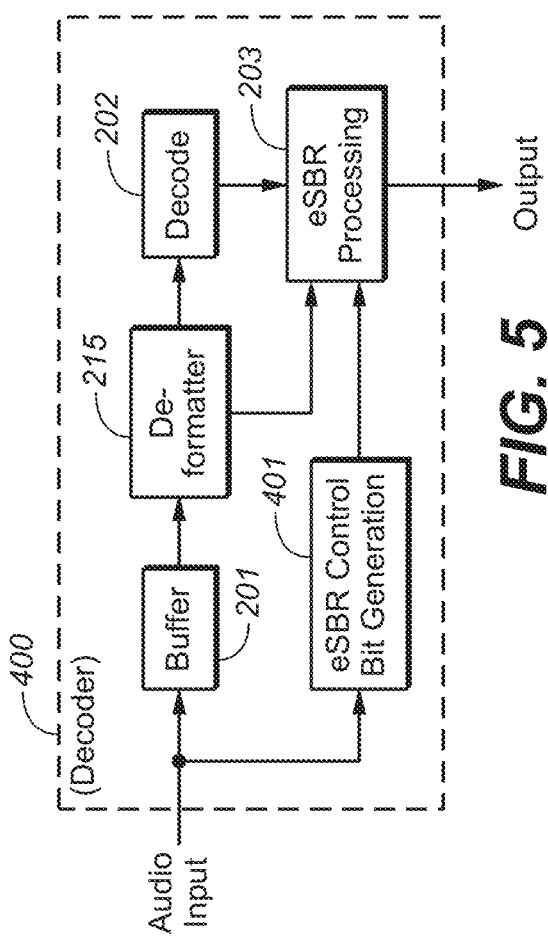
FIG. 5 is a block diagram of a decoder which is another embodiment of the inventive audio processing unit.

The eSBR decoder (400) of FIG. 5 includes buffer memory 201 (which is identical to memory 201 of FIGS. 3 and 4), bitstream payload deformatter 215 (which is identical to deformatter 215 of FIG. 4), audio decoding subsystem 202 (sometimes referred to as a "core" decoding stage or "core" decoding subsystem, and which is identical to core decoding subsystem 202 of FIG. 3), eSBR control data generation subsystem 401, and eSBR processing stage 203 (which is identical to stage 203 of FIG. 3), connected as shown. Typically also, decoder 400 includes other processing elements (not shown).

In operation of decoder 400, a sequence of blocks of an encoded audio bitstream (an MPEG-4 AAC bitstream) received by decoder 400 is asserted from buffer 201 to deformatter 215.

Deformatter 215 is coupled and configured to demultiplex each block of the bitstream to extract SBR metadata (including quantized envelope data) and typically also other metadata therefrom. Deformatter 215 is configured to assert at least the SBR metadata to eSBR processing stage 203. Deformatter 215 is also coupled and configured to extract audio data from each block of the bitstream, and to assert the extracted audio data to decoding subsystem (decoding stage) 202.

Audio decoding subsystem 202 of decoder 400 is configured to decode the audio data extracted by deformatter 215 (such decoding may be referred to as a "core" decoding operation) to generate decoded audio data, and to assert the decoded audio data to eSBR processing stage 203. The decoding is performed in the frequency domain. Typically, a final stage of processing in subsystem 202 applies a frequency domain-to-time domain transform to the decoded frequency domain audio data, so that the output of subsystem is time domain, decoded audio data. Stage 203 is configured to apply SBR tools (and eSBR tools) indicated by the SBR metadata (extracted by deformatter 215) and by eSBR metadata generated in subsystem 401, to the decoded audio data (i.e., to perform SBR and eSBR processing on the output of decoding subsystem 202 using the SBR and eSBR metadata) to generate the fully decoded audio data which is output from decoder 400. Typically, decoder 400 includes a memory (accessible by subsystem 202 and stage 203) which stores the deformatted audio data and metadata output from deformatter 215 (and optionally also subsystem 401), and stage 203 is configured to access the audio data and metadata as needed during SBR and eSBR processing. The SBR processing in stage 203 may be considered to be post-processing on the output of core decoding subsystem 202. Optionally, decoder 400 also includes a final upmixing subsystem (which may apply parametric stereo ("PS") tools defined in the MPEG-4 AAC standard, using PS metadata extracted by deformatter 215) which is coupled and configured to perform upmixing on the output of stage 203 to generated fully decoded, upmixed audio which is output from APU 210.

Parametric stereo is a coding tool that represents a stereo signal using a linear downmix of the left and right channels of the stereo signal and sets of spatial parameters describing the stereo image. Parametric stereo typically employs three types of spatial parameters: (1) inter-channel intensity differences (IID) describing the intensity differences between the channels; (2) inter-channel phase differences (IPD) describing the phase differences between the channels; and (3) inter-channel coherence (ICC) describing the coherence (or similarity) between the channels. The coherence may be measured as the maximum of the cross-correlation as a function of time or phase. These three parameters generally enable a high quality reconstruction of the stereo image. However, the IPD parameters only specify the relative phase differences between the channels of the stereo input signal and do not indicate the distribution of these phase differences over the left and right channels. Therefore, a fourth type of parameter describing an overall phase offset or overall phase difference (OPD) may additionally be used. In the stereo reconstruction process, consecutive windowed segments of both the received downmix signal, s [n], and a decorrelated version of the received downmix, d [n], are processed together with the spatial parameters to generate the left ($l_k(n)$) and right ($r_k(n)$) reconstructed signals according to:

$$l_k(n)=H_{11}(k,n)s_k(n)+H_{21}(k,n)d_k(n)$$

$$r_k(n)=H_{12}(k,n)s_k(n)+H_{22}(k,n)d_k(n)$$

where $H_{11}$, $H_{12}$, $H_{21}$ and $H_{22}$ are defined by the stereo parameters. The signals $l_k(n)$ and $r_k(n)$ are finally transformed back to the time domain by means of a frequency-to-time transform.

Control data generation subsystem 401 of FIG. 5 is coupled and configured to detect at least one property of the encoded audio bitstream to be decoded, and to generate eSBR control data (which may be or include eSBR metadata of any of the types included in encoded audio bitstreams in accordance with other embodiments of the invention) in response to at least one result of the detection step. The eSBR control data is asserted to stage 203 to trigger application of individual eSBR tools or combinations of eSBR tools upon detecting a specific property (or combination of properties) of the bitstream, and/or to control the application of such eSBR tools. For example, in order to control performance of eSBR processing using harmonic transposition, some embodiments of control data generation subsystem 401 would include: a music detector (e.g., a simplified version of a conventional music detector) for setting the sbrPatchingMode [ch] parameter (and asserting the set parameter to stage 203) in response to detecting that the bitstream is or is not indicative of music; a transient detector for setting the sbrOversamplingFlag [ch] parameter (and asserting the set parameter to stage 203) in response to detecting the presence or absence of transients in the audio content indicated by the bitstream; and/or a pitch detector for setting the sbrPitchInBinsFlag [ch] and sbrPitchInBins [ch] parameters (and asserting the set parameters to stage 203) in response to detecting the pitch of audio content indicated by the bitstream. Other aspects of the invention are audio bitstream decoding methods performed by any embodiment of the inventive decoder described in this paragraph and the preceding paragraph.

Aspects of the invention include an encoding or decoding method of the type which any embodiment of the inventive APU, system or device is configured (e.g., programmed) to perform. Other aspects of the invention include a system or device configured (e.g., programmed) to perform any embodiment of the inventive method, and a computer readable medium (e.g., a disc) which stores code (e.g., in a non-transitory manner) for implementing any embodiment of the inventive method or steps thereof. For example, the inventive system can be or include a programmable general purpose processor, digital signal processor, or microprocessor, programmed with software or firmware and/or otherwise configured to perform any of a variety of operations on data, including an embodiment of the inventive method or steps thereof. Such a general purpose processor may be or include a computer system including an input device, a memory, and processing circuitry programmed (and/or otherwise configured) to perform an embodiment of the inventive method (or steps thereof) in response to data asserted thereto.

Embodiments of the present invention may be implemented in hardware, firmware, or software, or a combination of both (e.g., as a programmable logic array). Unless otherwise specified, the algorithms or processes included as part of the invention are not inherently related to any particular computer or other apparatus. In particular, various general-purpose machines may be used with programs written in accordance with the teachings herein, or it may be more convenient to construct more specialized apparatus (e.g., integrated circuits) to perform the required method steps. Thus, the invention may be implemented in one or more computer programs executing on one or more programmable computer systems (e.g., an implementation of any of the elements of FIG. 1, or encoder 100 of FIG. 2 (or an element thereof), or decoder 200 of FIG. 3 (or an element thereof), or decoder 210 of FIG. 4 (or an element thereof), or decoder 400 of FIG. 5 (or an element thereof)) each comprising at least one processor, at least one data storage system (including volatile and non-volatile memory and/or storage elements), at least one input device or port, and at least one output device or port. Program code is applied to input data to perform the functions described herein and generate output information. The output information is applied to one or more output devices, in known fashion.

Each such program may be implemented in any desired computer language (including machine, assembly, or high level procedural, logical, or object oriented programming languages) to communicate with a computer system. In any case, the language may be a compiled or interpreted language.

For example, when implemented by computer software instruction sequences, various functions and steps of embodiments of the invention may be implemented by multithreaded software instruction sequences running in suitable digital signal processing hardware, in which case the various devices, steps, and functions of the embodiments may correspond to portions of the software instructions.

Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be implemented as a computer-readable storage medium, configured with (i.e., storing) a computer program, where the storage medium so configured causes a computer system to operate in a specific and predefined manner to perform the functions described herein.

A number of embodiments of the invention have been described. Nevertheless, it will be understood that various modifications may be made without departing from the spirit and scope of the invention. Numerous modifications and variations of the present invention are possible in light of the above teachings. For example, in order to facilitate efficient implementations, phase-shifts may be used in combination with the complex QMF analysis and synthesis filter banks. The analysis filterbank is responsible for filtering the time-domain lowband signal generated by the core decoder into a plurality of subbands (e.g., QMF subbands). The synthesis filterbank is responsible for combining the regenerated highband produced by the selected HFR technique (as indicated by the received sbrPatchingMode parameter) with the decoded lowband to produce a wideband output audio signal. A given filterbank implementation operating in a certain sample-rate mode, e.g., normal dual-rate operation or down-sampled SBR mode, should not, however, have phase-shifts that are bitstream dependent. The QMF banks used in SBR are a complex-exponential extension of the theory of cosine modulated filter banks. It can be shown that alias cancellation constraints become obsolete when extending the cosine modulated filterbank with complex-exponential modulation. Thus, for the SBR QMF banks, both the analysis filters, $h_k(n)$, and synthesis filters, $f_k(n)$, may be defined by:

$$h_k(n) = f_k(n) = p_0(n)\exp\left\{i\frac{\pi}{M}\left(k+\frac{1}{2}\right)\left(n-\frac{N}{2}\right)\right\}, 0 \le n \le N; 0 \le k < M$$

where $p_0(n)$ is a real-valued symmetric or asymmetric prototype filter (typically, a low-pass prototype filter), M denotes the number of channels and N is the prototype filter order. The number of channels used in the analysis filterbank may be different than the number of channel used in the synthesis filterbank. For example, the analysis filterbank may have 32 channels and the synthesis filterbank may have 64 channels. When operating the synthesis filterbank in down-sampled mode, the synthesis filterbank may have only 32 channels. Since the subband samples from the filter bank are complex-valued, an additive possibly channel-dependent phase-shift step may be appended to the analysis filterbank. These extra phase-shifts need to be compensated for before the synthesis filter bank. While the phase-shifting terms in principle can be of arbitrary values without destroying the operation of the QMF analysis/synthesis-chain, they may also be constrained to certain values for conformance verification. The SBR signal will be affected by the choice of the phase factors while the low pass signal coming from the core decoder will not. The audio quality of the output signal is not affected.

The coefficients of the prototype filter, $p_0(n)$, may be defined with a length, L, of 640, as shown in Table 4 below.

TABLE 4

| n | $p_0(n)$ |
|---|---|
| 0 | 0.0000000000 |
| 1 | −0.0005525286 |
| 2 | −0.0005617692 |
| 3 | −0.0004947518 |
| 4 | −0.0004875227 |
| 5 | −0.0004893791 |
| 6 | −0.0005040714 |
| 7 | −0.0005226564 |
| 8 | −0.0005466565 |
| 9 | −0.0005677802 |
| 10 | −0.0005870930 |
| 11 | −0.0006132747 |
| 12 | −0.0006312493 |
| 13 | −0.0006540333 |
| 14 | −0.0006777690 |
| 15 | −0.0006941614 |
| 16 | −0.0007157736 |
| 17 | −0.0007255043 |

TABLE 4-continued

| n | $p_0(n)$ |
|---|---|
| 18 | −0.0007440941 |
| 19 | −0.0007490598 |
| 20 | −0.0007681371 |
| 21 | −0.0007724848 |
| 22 | −0.0007834332 |
| 23 | −0.0007779869 |
| 24 | −0.0007803664 |
| 25 | −0.0007801449 |
| 26 | −0.0007757977 |
| 27 | −0.0007630793 |
| 28 | −0.0007530001 |
| 29 | −0.0007319357 |
| 30 | −0.0007215391 |
| 31 | −0.0006917937 |
| 32 | −0.0006650415 |
| 33 | −0.0006341594 |
| 34 | −0.0005946118 |
| 35 | −0.0005564576 |
| 36 | −0.0005145572 |
| 37 | −0.0004606325 |
| 38 | 0.0004095121 |
| 39 | −0.0003501175 |
| 40 | −0.0002896981 |
| 41 | −0.0002098337 |
| 42 | −0.0001446380 |
| 43 | −0.0000617334 |
| 44 | 0.0000134949 |
| 45 | 0.0001094383 |
| 46 | 0.0002043017 |
| 47 | 0.0002949531 |
| 48 | 0.0004026540 |
| 49 | 0.0005107388 |
| 50 | 0.0006239376 |
| 51 | 0.0007458025 |
| 52 | 0.0008608443 |
| 53 | 0.0009885988 |
| 54 | 0.0011250155 |
| 55 | 0.0012577884 |
| 56 | 0.0013902494 |
| 57 | 0.0015443219 |
| 58 | 0.0016868083 |
| 59 | 0.0018348265 |
| 60 | 0.0019841140 |
| 61 | 0.0021461583 |
| 62 | 0.0023017254 |
| 63 | 0.0024625616 |
| 64 | 0.0026201758 |
| 65 | 0.0027870464 |
| 66 | 0.0029469447 |
| 67 | 0.0031125420 |
| 68 | 0.0032739613 |
| 69 | 0.0034418874 |
| 70 | 0.0036008268 |
| 71 | 0.0037603922 |
| 72 | 0.0039207432 |
| 73 | 0.0040819753 |
| 74 | 0.0042264269 |
| 75 | 0.0043730719 |
| 76 | 0.0045209852 |
| 77 | 0.0046606460 |
| 78 | 0.0047932560 |
| 79 | 0.0049137603 |
| 80 | 0.0050393022 |
| 81 | 0.0051407353 |
| 82 | 0.0052461166 |
| 83 | 0.0053471681 |
| 84 | 0.0054196775 |
| 85 | 0.0054876040 |
| 86 | 0.0055475714 |
| 87 | 0.0055938023 |
| 88 | 0.0056220643 |
| 89 | 0.0056455196 |
| 90 | 0.0056389199 |
| 91 | 0.0056266114 |
| 92 | 0.0055917128 |
| 93 | 0.0055404363 |
| 94 | 0.0054753783 |
| 95 | 0.0053838975 |
| 96 | 0.0052715758 |
| 97 | 0.0051382275 |
| 98 | 0.0049839687 |
| 99 | 0.0048109469 |
| 100 | 0.0046039530 |
| 101 | 0.0043801861 |
| 102 | 0.0041251642 |
| 103 | 0.0038456408 |
| 104 | 0.0035401246 |
| 105 | 0.0032091885 |
| 106 | 0.0028446757 |
| 107 | 0.0024508540 |
| 108 | 0.0020274176 |
| 109 | 0.0015784682 |
| 110 | 0.0010902329 |
| 111 | 0.0005832264 |
| 112 | 0.0000276045 |
| 113 | −0.0005464280 |
| 114 | −0.0011568135 |
| 115 | −0.0018039472 |
| 116 | −0.0024826723 |
| 117 | −0.0031933778 |
| 118 | −0.0039401124 |
| 119 | −0.0047222596 |
| 120 | −0.0055337211 |
| 121 | −0.0063792293 |
| 122 | −0.0072615816 |
| 123 | −0.0081798233 |
| 124 | −0.0091325329 |
| 125 | −0.0101150215 |
| 126 | −0.0111315548 |
| 127 | −0.0121849995 |
| 128 | 0.0132718220 |
| 129 | 0.0143904666 |
| 130 | 0.0155405553 |
| 131 | 0.0167324712 |
| 132 | 0.0179433381 |
| 133 | 0.0191872431 |
| 134 | 0.0204531793 |
| 135 | 0.0217467550 |
| 136 | 0.0230680169 |
| 137 | 0.0244160992 |
| 138 | 0.0257875847 |
| 139 | 0.0271859429 |
| 140 | 0.0286072173 |
| 141 | 0.0300502657 |
| 142 | 0.0315017608 |
| 143 | 0.0329754081 |
| 144 | 0.0344620948 |
| 145 | 0.0359697560 |
| 146 | 0.0374812850 |
| 147 | 0.0390053679 |
| 148 | 0.0405349170 |
| 149 | 0.0420649094 |
| 150 | 0.0436097542 |
| 151 | 0.0451488405 |
| 152 | 0.0466843027 |
| 153 | 0.0482165720 |
| 154 | 0.0497385755 |
| 155 | 0.0512556155 |
| 156 | 0.0527630746 |
| 157 | 0.0542452768 |
| 158 | 0.0557173648 |
| 159 | 0.0571616450 |
| 160 | 0.0585915683 |
| 161 | 0.0599837480 |
| 162 | 0.0613455171 |
| 163 | 0.0626857808 |
| 164 | 0.0639715898 |
| 165 | 0.0652247106 |
| 166 | 0.0664367512 |
| 167 | 0.0676075985 |
| 168 | 0.0687043828 |
| 169 | 0.0697630244 |
| 170 | 0.0707628710 |
| 171 | 0.0717002673 |
| 172 | 0.0725682583 |
| 173 | 0.0733620255 |

TABLE 4-continued

| n | p₀(n) |
|---|---|
| 174 | 0.0741003642 |
| 175 | 0.0747452558 |
| 176 | 0.0753137336 |
| 177 | 0.0758008358 |
| 178 | 0.0761992479 |
| 179 | 0.0764992170 |
| 180 | 0.0767093490 |
| 181 | 0.0768173975 |
| 182 | 0.0768230011 |
| 183 | 0.0767204924 |
| 184 | 0.0765050718 |
| 185 | 0.0761748321 |
| 186 | 0.0757305756 |
| 187 | 0.0751576255 |
| 188 | 0.0744664394 |
| 189 | 0.0736406005 |
| 190 | 0.0726774642 |
| 191 | 0.0715826364 |
| 192 | 0.0703533073 |
| 193 | 0.0689664013 |
| 194 | 0.0674525021 |
| 195 | 0.0657690668 |
| 196 | 0.0639444805 |
| 197 | 0.0619602779 |
| 198 | 0.0598166570 |
| 199 | 0.0575152691 |
| 200 | 0.0550460034 |
| 201 | 0.0524093821 |
| 202 | 0.0495978676 |
| 203 | 0.0466303305 |
| 204 | 0.0434768782 |
| 205 | 0.0401458278 |
| 206 | 0.0366418116 |
| 207 | 0.0329583930 |
| 208 | 0.0290824006 |
| 209 | 0.0250307561 |
| 210 | 0.0207997072 |
| 211 | 0.0163701258 |
| 212 | 0.0117623832 |
| 213 | 0.0069636862 |
| 214 | 0.0019765601 |
| 215 | −0.0032086896 |
| 216 | −0.0085711749 |
| 217 | −0.0141288827 |
| 218 | −0.0198834129 |
| 219 | −0.0258227288 |
| 220 | −0.0319531274 |
| 221 | −0.0382776572 |
| 222 | −0.0447806821 |
| 223 | −0.0514804176 |
| 224 | −0.0583705326 |
| 225 | −0.0654409853 |
| 226 | −0.0726943300 |
| 227 | −0.0801372934 |
| 228 | −0.0877547536 |
| 229 | −0.0955533352 |
| 230 | −0.1035329531 |
| 231 | −0.1116826931 |
| 232 | −0.1200077984 |
| 233 | −0.1285002850 |
| 234 | −0.1371551761 |
| 235 | −0.1459766491 |
| 236 | −0.1549607071 |
| 237 | −0.1640958855 |
| 238 | −0.1733808172 |
| 239 | −0.1828172548 |
| 240 | −0.1923966745 |
| 241 | −0.2021250176 |
| 242 | −0.2119735853 |
| 243 | −0.2219652696 |
| 244 | −0.2320690870 |
| 245 | −0.2423016884 |
| 246 | −0.2526480309 |
| 247 | −0.2631053299 |
| 248 | −0.2736634040 |
| 249 | −0.2843214189 |
| 250 | −0.2950716717 |
| 251 | −0.3059098575 |

TABLE 4-continued

| n | p₀(n) |
|---|---|
| 252 | −0.3168278913 |
| 253 | −0.3278113727 |
| 254 | −0.3388722693 |
| 255 | −0.3499914122 |
| 256 | 0.3611589903 |
| 257 | 0.3723795546 |
| 258 | 0.3836350013 |
| 259 | 0.3949211761 |
| 260 | 0.4062317676 |
| 261 | 0.4175696896 |
| 262 | 0.4289119920 |
| 263 | 0.4402553754 |
| 264 | 0.4515996535 |
| 265 | 0.4629308085 |
| 266 | 0.4742453214 |
| 267 | 0.4855253091 |
| 268 | 0.4967708254 |
| 269 | 0.5079817500 |
| 270 | 0.5191234970 |
| 271 | 0.5302240895 |
| 272 | 0.5412553448 |
| 273 | 0.5522051258 |
| 274 | 0.5630789140 |
| 275 | 0.5738524131 |
| 276 | 0.5845403235 |
| 277 | 0.5951123086 |
| 278 | 0.6055783538 |
| 279 | 0.6159109932 |
| 280 | 0.6261242695 |
| 281 | 0.6361980107 |
| 282 | 0.6461269695 |
| 283 | 0.6559016302 |
| 284 | 0.6655139880 |
| 285 | 0.6749663190 |
| 286 | 0.6842353293 |
| 287 | 0.6933282376 |
| 288 | 0.7022388719 |
| 289 | 0.7109410426 |
| 290 | 0.7194462634 |
| 291 | 0.7277448900 |
| 292 | 0.7358211758 |
| 293 | 0.7436827863 |
| 294 | 0.7513137456 |
| 295 | 0.7587080760 |
| 296 | 0.7658674865 |
| 297 | 0.7727780881 |
| 298 | 0.7794287519 |
| 299 | 0.7858353120 |
| 300 | 0.7919735841 |
| 301 | 0.7978466413 |
| 302 | 0.8034485751 |
| 303 | 0.8087695004 |
| 304 | 0.8138191270 |
| 305 | 0.8185776004 |
| 306 | 0.8230419890 |
| 307 | 0.8272275347 |
| 308 | 0.8311038457 |
| 309 | 0.8346937361 |
| 310 | 0.8379717337 |
| 311 | 0.8409541392 |
| 312 | 0.8436238281 |
| 313 | 0.8459818469 |
| 314 | 0.8480315777 |
| 315 | 0.8497805198 |
| 316 | 0.8511971524 |
| 317 | 0.8523047035 |
| 318 | 0.8531020949 |
| 319 | 0.8535720573 |
| 320 | 0.8537385600 |
| 321 | 0.8535720573 |
| 322 | 0.8531020949 |
| 323 | 0.8523047035 |
| 324 | 0.8511971524 |
| 325 | 0.8497805198 |
| 326 | 0.8480315777 |
| 327 | 0.8459818469 |
| 328 | 0.8436238281 |
| 329 | 0.8409541392 |

TABLE 4-continued

| n | $p_0(n)$ |
|---|---|
| 330 | 0.8379717337 |
| 331 | 0.8346937361 |
| 332 | 0.8311038457 |
| 333 | 0.8272275347 |
| 334 | 0.8230419890 |
| 335 | 0.8185776004 |
| 336 | 0.8138191270 |
| 337 | 0.8087695004 |
| 338 | 0.8034485751 |
| 339 | 0.7978466413 |
| 340 | 0.7919735841 |
| 341 | 0.7858353120 |
| 342 | 0.7794287519 |
| 343 | 0.7727780881 |
| 344 | 0.7658674865 |
| 345 | 0.7587080760 |
| 346 | 0.7513137456 |
| 347 | 0.7436827863 |
| 348 | 0.7358211758 |
| 349 | 0.7277448900 |
| 350 | 0.7194462634 |
| 351 | 0.7109410426 |
| 352 | 0.7022388719 |
| 353 | 0.6933282376 |
| 354 | 0.6842353293 |
| 355 | 0.6749663190 |
| 356 | 0.6655139880 |
| 357 | 0.6559016302 |
| 358 | 0.6461269695 |
| 359 | 0.6361980107 |
| 360 | 0.6261242695 |
| 361 | 0.6159109932 |
| 362 | 0.6055783538 |
| 363 | 0.5951123086 |
| 364 | 0.5845403235 |
| 365 | 0.5738524131 |
| 366 | 0.5630789140 |
| 367 | 0.5522051258 |
| 368 | 0.5412553448 |
| 369 | 0.5302240895 |
| 370 | 0.5191234970 |
| 371 | 0.5079817500 |
| 372 | 0.4967708254 |
| 373 | 0.4855253091 |
| 374 | 0.4742453214 |
| 375 | 0.4629308085 |
| 376 | 0.4515996535 |
| 377 | 0.4402553754 |
| 378 | 0.4289119920 |
| 379 | 0.4175696896 |
| 380 | 0.4062317676 |
| 381 | 0.3949211761 |
| 382 | 0.3836350013 |
| 383 | 0.3723795546 |
| 384 | −0.3611589903 |
| 385 | −0.3499914122 |
| 386 | −0.3388722693 |
| 387 | −0.3278113727 |
| 388 | −0.3168278913 |
| 389 | −0.3059098575 |
| 390 | 0.2950716717 |
| 391 | −0.2843214189 |
| 392 | −0.2736634040 |
| 393 | −0.2631053299 |
| 394 | −0.2526480309 |
| 395 | −0.2423016884 |
| 396 | −0.2320690870 |
| 397 | −0.2219652696 |
| 398 | −0.2119735853 |
| 399 | −0.2021250176 |
| 400 | −0.1923966745 |
| 401 | −0.1828172548 |
| 402 | −0.1733808172 |
| 403 | −0.1640958855 |
| 404 | −0.1549607071 |
| 405 | −0.1459766491 |
| 406 | −0.1371551761 |
| 407 | −0.1285002850 |
| 408 | −0.1200077984 |
| 409 | −0.1116826931 |
| 410 | −0.1035329531 |
| 411 | −0.0955533352 |
| 412 | −0.0877547536 |
| 413 | −0.0801372934 |
| 414 | 0.0726943300 |
| 415 | −0.0654409853 |
| 416 | −0.0583705326 |
| 417 | −0.0514804176 |
| 418 | −0.0447806821 |
| 419 | −0.0382776572 |
| 420 | −0.0319531274 |
| 421 | −0.0258227288 |
| 422 | −0.0198834129 |
| 423 | −0.0141288827 |
| 424 | −0.0085711749 |
| 425 | −0.0032086896 |
| 426 | 0.0019765601 |
| 427 | 0.0069636862 |
| 428 | 0.0117623832 |
| 429 | 0.0163701258 |
| 430 | 0.0207997072 |
| 431 | 0.0250307561 |
| 432 | 0.0290824006 |
| 433 | 0.0329583930 |
| 434 | 0.0366418116 |
| 435 | 0.0401458278 |
| 436 | 0.0434768782 |
| 437 | 0.0466303305 |
| 438 | 0.0495978676 |
| 439 | 0.0524093821 |
| 440 | 0.0550460034 |
| 441 | 0.0575152691 |
| 442 | 0.0598166570 |
| 443 | 0.0619602779 |
| 444 | 0.0639444805 |
| 445 | 0.0657690668 |
| 446 | 0.0674525021 |
| 447 | 0.0689664013 |
| 448 | 0.0703533073 |
| 449 | 0.0715826364 |
| 450 | 0.0726774642 |
| 451 | 0.0736406005 |
| 452 | 0.0744664394 |
| 453 | 0.0751576255 |
| 454 | 0.0757305756 |
| 455 | 0.0761748321 |
| 456 | 0.0765050718 |
| 457 | 0.0767204924 |
| 458 | 0.0768230011 |
| 459 | 0.0768173975 |
| 460 | 0.0767093490 |
| 461 | 0.0764992170 |
| 462 | 0.0761992479 |
| 463 | 0.0758008358 |
| 464 | 0.0753137336 |
| 465 | 0.0747452558 |
| 466 | 0.0741003642 |
| 467 | 0.0733620255 |
| 468 | 0.0725682583 |
| 469 | 0.0717002673 |
| 470 | 0.0707628710 |
| 471 | 0.0697630244 |
| 472 | 0.0687043828 |
| 473 | 0.0676075985 |
| 474 | 0.0664367512 |
| 475 | 0.0652247106 |
| 476 | 0.0639715898 |
| 477 | 0.0626857808 |
| 478 | 0.0613455171 |
| 479 | 0.0599837480 |
| 480 | 0.0585915683 |
| 481 | 0.0571616450 |
| 482 | 0.0557173648 |
| 483 | 0.0542452768 |
| 484 | 0.0527630746 |
| 485 | 0.0512556155 |

TABLE 4-continued

| n | $p_0(n)$ |
|---|---|
| 486 | 0.0497385755 |
| 487 | 0.0482165720 |
| 488 | 0.0466843027 |
| 489 | 0.0451488405 |
| 490 | 0.0436097542 |
| 491 | 0.0420649094 |
| 492 | 0.0405349170 |
| 493 | 0.0390053679 |
| 494 | 0.0374812850 |
| 495 | 0.0359697560 |
| 496 | 0.0344620948 |
| 497 | 0.0329754081 |
| 498 | 0.0315017608 |
| 499 | 0.0300502657 |
| 500 | 0.0286072173 |
| 501 | 0.0271859429 |
| 502 | 0.0257875847 |
| 503 | 0.0244160992 |
| 504 | 0.0230680169 |
| 505 | 0.0217467550 |
| 506 | 0.0204531793 |
| 507 | 0.0191872431 |
| 508 | 0.0179433381 |
| 509 | 0.0167324712 |
| 510 | 0.0155405553 |
| 511 | 0.0143904666 |
| 512 | −0.0132718220 |
| 513 | −0.0121849995 |
| 514 | −0.0111315548 |
| 515 | −0.0101150215 |
| 516 | −0.0091325329 |
| 517 | −0.0081798233 |
| 518 | −0.0072615816 |
| 519 | −0.0063792293 |
| 520 | −0.0055337211 |
| 521 | 0.0047222596 |
| 522 | −0.0039401124 |
| 523 | −0.0031933778 |
| 524 | −0.0024826723 |
| 525 | −0.0018039472 |
| 526 | −0.0011568135 |
| 527 | −0.0005464280 |
| 528 | 0.0000276045 |
| 529 | 0.0005832264 |
| 530 | 0.0010902329 |
| 531 | 0.0015784682 |
| 532 | 0.0020274176 |
| 533 | 0.0024508540 |
| 534 | 0.0028446757 |
| 535 | 0.0032091885 |
| 536 | 0.0035401246 |
| 537 | 0.0038456408 |
| 538 | 0.0041251642 |
| 539 | 0.0043801861 |
| 540 | 0.0046039530 |
| 541 | 0.0048109469 |
| 542 | 0.0049839687 |
| 543 | 0.0051382275 |
| 544 | 0.0052715758 |
| 545 | 0.0053838975 |
| 546 | 0.0054753783 |
| 547 | 0.0055404363 |
| 548 | 0.0055917128 |
| 549 | 0.0056266114 |
| 550 | 0.0056389199 |
| 551 | 0.0056455196 |
| 552 | 0.0056220643 |
| 553 | 0.0055938023 |
| 554 | 0.0055475714 |
| 555 | 0.0054876040 |
| 556 | 0.0054196775 |
| 557 | 0.0053471681 |
| 558 | 0.0052461166 |
| 559 | 0.0051407353 |
| 560 | 0.0050393022 |
| 561 | 0.0049137603 |
| 562 | 0.0047932560 |
| 563 | 0.0046606460 |
| 564 | 0.0045209852 |
| 565 | 0.0043730719 |
| 566 | 0.0042264269 |
| 567 | 0.0040819753 |
| 568 | 0.0039207432 |
| 569 | 0.0037603922 |
| 570 | 0.0036008268 |
| 571 | 0.0034418874 |
| 572 | 0.0032739613 |
| 573 | 0.0031125420 |
| 574 | 0.0029469447 |
| 575 | 0.0027870464 |
| 576 | 0.0026201758 |
| 577 | 0.0024625616 |
| 578 | 0.0023017254 |
| 579 | 0.0021461583 |
| 580 | 0.0019841140 |
| 581 | 0.0018348265 |
| 582 | 0.0016868083 |
| 583 | 0.0015443219 |
| 584 | 0.0013902494 |
| 585 | 0.0012577884 |
| 586 | 0.0011250155 |
| 587 | 0.0009885988 |
| 588 | 0.0008608443 |
| 589 | 0.0007458025 |
| 590 | 0.0006239376 |
| 591 | 0.0005107388 |
| 592 | 0.0004026540 |
| 593 | 0.0002949531 |
| 594 | 0.0002043017 |
| 595 | 0.0001094383 |
| 596 | 0.0000134949 |
| 597 | −0.0000617334 |
| 598 | −0.0001446380 |
| 599 | −0.0002098337 |
| 600 | −0.0002896981 |
| 601 | −0.0003501175 |
| 602 | −0.0004095121 |
| 603 | −0.0004606325 |
| 604 | −0.0005145572 |
| 605 | −0.0005564576 |
| 606 | −0.0005946118 |
| 607 | −0.0006341594 |
| 608 | −0.0006650415 |
| 609 | −0.0006917937 |
| 610 | −0.0007215391 |
| 611 | −0.0007319357 |
| 612 | −0.0007530001 |
| 613 | −0.0007630793 |
| 614 | −0.0007757977 |
| 615 | −0.0007801449 |
| 616 | −0.0007803664 |
| 617 | −0.0007779869 |
| 618 | −0.0007834332 |
| 619 | −0.0007724848 |
| 620 | −0.0007681371 |
| 621 | −0.0007490598 |
| 622 | −0.0007440941 |
| 623 | −0.0007255043 |
| 624 | −0.0007157736 |
| 625 | −0.0006941614 |
| 626 | −0.0006777690 |
| 627 | −0.0006540333 |
| 628 | −0.0006312493 |
| 629 | −0.0006132747 |
| 630 | −0.0005870930 |
| 631 | −0.0005677802 |
| 632 | −0.0005466565 |
| 633 | −0.0005226564 |
| 634 | −0.0005040714 |
| 635 | −0.0004893791 |
| 636 | −0.0004875227 |
| 637 | −0.0004947518 |
| 638 | −0.0005617692 |
| 639 | −0.0005525280 |

The prototype filter, $p_0(n)$, may also be derived from Table 4 by one or more mathematical operations such as rounding, subsampling, interpolation, and decimation.

Although the tuning of SBR related control information does not typically depend of the details of the transposition (as previously discussed), in some embodiments certain elements of the control data may be simulcasted in the eSBR extension container (bs_extension_id==EXTENSION_ID_ESBR) to improve the quality of the regenerated signal. Some of the simulcasted elements may include the noise floor data (for example, noise floor scale factors and a parameter indicating the direction, either in the frequency or time direction, of delta coding for each noise floor), the inverse filtering data (for example, a parameter indicating the inverse filtering mode selected from no inverse filtering, a low level of inverse filtering, an intermediate level of inverse filtering, and a strong level of inverse filtering), and the missing harmonics data (for example, a parameter indicating whether a sinusoid should be added to a specific frequency band of the regenerated highband). All of these elements rely on a synthesized emulation of the decoder's transposer performed in the encoder and therefore if properly tuned for the selected transposer may increase the quality of the regenerated signal.

Specifically, in some embodiments, the missing harmonics and inverse filtering control data is transmitted in the eSBR extension container (along with the other bitstream parameters of Table 3) and tuned for the harmonic transposer of eSBR. The additional bitrate required to transmit these two classes of metadata for the harmonic transposer of eSBR is relatively low. Therefore, sending tuned missing harmonic and/or inverse filtering control data in the cSBR extension container will increase the quality of audio produced by the transposer while only minimally affecting bitrate. To ensure backward-compatibility with legacy decoders, the parameters tuned for the spectral translation operation of SBR may also be sent in the bitstream as part of the SBR control data using either implicit or explicit signaling.

Complexity of a decoder with the SBR enhancements as described in this application must be limited to not significantly increase the overall computational complexity of the implementation. Preferably, the PCU (MOP) for the SBR object type is at or below 4.5 when using the cSBR tool, and the RCU for the SBR object type is at or below 3 when using the cSBR tool. The approximated processing power is given in Processor Complexity Units (PCU), specified in integer numbers of MOPS. The approximated RAM usage is given in RAM Complexity Units (RCU), specified in integer numbers of kWords (1000 words). The RCU numbers do not include working buffers that can be shared between different objects and/or channels. Also, the PCU is proportional to sampling frequency. PCU values are given in MOPS (Million Operations per Second) per channel, and RCU values in kWords per channel.

For compressed data, like HE-AAC coded audio, which can be decoded by different decoder configurations, special attention is needed. In this case, decoding can be done in a backward-compatible fashion (AAC only) as well as in an enhanced fashion (AAC+SBR). If compressed data permits both backward-compatible and enhanced decoding, and if the decoder is operating in enhanced fashion such that it is using a post-processor that inserts some additional delay (e.g., the SBR post-processor in HE-AAC), then it must insure that this additional time delay incurred relative to the backwards-compatible mode, as described by a corresponding value of n, is taken into account when presenting the composition unit. In order to ensure that composition time stamps are handled correctly (so that audio remains synchronized with other media), the additional delay introduced by the post-processing given in number of samples (per audio channel) at the output sample rate is 3010 when the decoder operation mode includes the SBR enhancements (including eSBR) as described in this application. Therefore, for an audio composition unit, the composition time applies to the 3011-th audio sample within the composition unit when the decoder operation mode includes the SBR enhancements as described in this application.

In order to improve the subjective quality for audio content with harmonic frequency structure and strong tonal characteristics, in particular at low bitrates, the SBR enhancements should be activated. The values of the corresponding bitstream element (i.e. esbr_data ( ), controlling these tools, may be determined in the encoder by applying a signal dependent classification mechanism.

Generally, the usage of the harmonic patching method (sbrPatchingMode==0) is preferable for coding music signals at very low bitrates, where the core codec may be considerably limited in audio bandwidth. This is especially true if these signals include a pronounced harmonic structure. Contrarily, the usage of the regular SBR patching method is preferred for speech and mixed signals, since it provides a better preservation of the temporal structure in speech.

In order to improve the performance of the MPEG-4 SBR transposer, a pre-processing step can be activated (bs_sbr_preprocessing==1) that avoids the introduction of spectral discontinuities of the signal going in to the subsequent envelope adjuster. The operation of the tool is beneficial for signal types where the coarse spectral envelope of the low band signal being used for high frequency reconstruction displays large variations in level.

In order to improve the transient response of the harmonic SBR patching (sbrPatchingMode==0), signal adaptive frequency domain oversampling can be applied (sbrOversamplingFlag==1). Since signal adaptive frequency domain oversampling increases the computational complexity of the transposer, but only brings benefits for frames which contain transients, the use of this tool is controlled by the bitstream element, which is transmitted once per frame and per independent SBR channel.

Typical bit rate settings recommendations for HE-AACv2 with SBR enhancements (that is, enabling the harmonic transposer of the eSBR tool) correspond to 20-32 kbps for stereo audio content at sampling rates of either 44.1 KHz or 48 kHz. The relative subjective quality gain of the SBR enhancements increases towards the lower bit rate boundary and a properly configured encoder allows to extend this range to even lower bit rates. The bit rates provided above are recommendations only and may be adapted for specific service requirements.

A decoder operating in the proposed enhanced SBR mode typically needs to be able to switch between legacy and enhanced SBR patching. Therefore, delay may be introduced which can be as long as the duration of one core audio frame, depending on decoder setup. Typically, the delay for both legacy and enhanced SBR patching will be similar.

It is to be understood that within the scope of the appended claims, the invention may be practiced otherwise than as specifically described herein. Any reference numerals contained in the following claims are for illustrative purposes only and should not be used to construe or limit the claims in any manner whatsoever.

Various aspects of the present invention may be appreciated from the following enumerated example embodiments (EEEs):

EEE 1. A method for performing high frequency reconstruction of an audio signal, the method comprising:
- receiving an encoded audio bitstream, the encoded audio bitstream including audio data representing a lowband portion of the audio signal and high frequency reconstruction metadata;
- decoding the audio data to generate a decoded lowband audio signal;
- extracting from the encoded audio bitstream the high frequency reconstruction metadata, the high frequency reconstruction metadata including operating parameters for a high frequency reconstruction process, the operating parameters including a patching mode parameter located in a backward-compatible extension container of the encoded audio bitstream, wherein a first value of the patching mode parameter indicates spectral translation and a second value of the patching mode parameter indicates harmonic transposition by phase-vocoder frequency spreading;
- filtering the decoded lowband audio signal to generate a filtered lowband audio signal;
- regenerating a highband portion of the audio signal using the filtered lowband audio signal and the high frequency reconstruction metadata, wherein the regenerating includes spectral translation if the patching mode parameter is the first value and the regenerating includes harmonic transposition by phase-vocoder frequency spreading if the patching mode parameter is the second value; and
- combining the filtered lowband audio signal with the regenerated highband portion to form a wideband audio signal,
- wherein the filtering, regenerating, and combining are performed as a post-processing operation with a delay of 3010 samples per audio channel or less, and wherein the spectral translation comprises maintaining a ratio between tonal and noise-like components by adaptive inverse filtering.

EEE 2. The method of EEE 1 wherein the encoded audio bitstream further includes a fill element with an identifier indicating a start of the fill element and fill data after the identifier, wherein the fill data includes the backward-compatible extension container.

EEE 3. The method of EEE 2 wherein the identifier is a three bit unsigned integer transmitted most significant bit first and having a value of 0x6.

EEE 4. The method of EEE 2 or EEE 3, wherein the fill data includes an extension payload, the extension payload includes spectral band replication extension data, and the extension payload is identified with a four bit unsigned integer transmitted most significant bit first and having a value of '1101' or '1110', and, optionally,
- wherein the spectral band replication extension data includes:
- an optional spectral band replication header,
- spectral band replication data after the header, and
- a spectral band replication extension element after the spectral band replication data, and wherein the flag is included in the spectral band replication extension element.

EEE 5. The method of any one of EEEs 1-4 wherein the high frequency reconstruction metadata includes envelope scale factors, noise floor scale factors, time/frequency grid information, or a parameter indicating a crossover frequency.

EEE 6. The method of any one of EEEs 1-5 wherein the backward-compatible extension container further includes a flag indicating whether additional preprocessing is used to avoid discontinuities in a shape of a spectral envelope of the highband portion when the patching mode parameter equals the first value, wherein a first value of the flag enables the additional preprocessing and a second value of the flag disables the additional preprocessing.

EEE 7. The method of EEE 6 wherein the additional preprocessing includes calculating a pre-gain curve using a linear prediction filter coefficient.

EEE 8. The method of any one of EEEs 1-5 wherein the backward-compatible extension container further includes a flag indicating whether signal adaptive frequency domain oversampling is to be applied when the patching mode parameter equals the second value, wherein a first value of the flag enables the signal adaptive frequency domain oversampling and a second value of the flag disables the signal adaptive frequency domain oversampling.

EEE 9. The method of EEE 8 wherein the signal adaptive frequency domain oversampling is applied only for frames containing a transient.

EEE 10. The method of any one of the previous EEEs wherein the harmonic transposition by phase-vocoder frequency spreading is performed with an estimated complexity at or below 4.5 million of operations per second and 3 kWords of memory.

EEE 11. A non-transitory computer readable medium containing instructions that when executed by a processor perform the method of any of the EEEs 1-10.

EEE 12. A computer program product having instructions which, when executed by a computing device or system, cause said computing device or system to execute the method of any of the EEEs 1-10.

EEE 13. An audio processing unit for performing high frequency reconstruction of an audio signal, the audio processing unit comprising:
- an input interface for receiving an encoded audio bitstream, the encoded audio bitstream including audio data representing a lowband portion of the audio signal and high frequency reconstruction metadata;
- a core audio decoder for decoding the audio data to generate a decoded lowband audio signal;
- a deformatter for extracting from the encoded audio bitstream the high frequency reconstruction metadata, the high frequency reconstruction metadata including operating parameters for a high frequency reconstruction process, the operating parameters including a patching mode parameter located in a backward-compatible extension container of the encoded audio bitstream, wherein a first value of the patching mode parameter indicates spectral translation and a second value of the patching mode parameter indicates harmonic transposition by phase-vocoder frequency spreading;
- an analysis filterbank for filtering the decoded lowband audio signal to generate a filtered lowband audio signal;
- a high frequency regenerator for reconstructing a highband portion of the audio signal using the filtered lowband audio signal and the high frequency reconstruction metadata, wherein the reconstructing includes a spectral translation if the patching mode parameter is the first value and the reconstructing includes harmonic transposition by phase-vocoder frequency spreading if the patching mode parameter is the second value; and a synthesis filterbank for combining the filtered lowband audio signal with the regenerated highband portion to form a wideband audio signal, wherein the analysis filterbank, high frequency regenerator, and synthesis filterbank are performed in a post-processor with a delay of 3010 samples per audio channel or less, and wherein the spectral translation comprises maintaining a ratio between tonal and noise-like components by adaptive inverse filtering.

EEE 14. The audio processing unit of EEE 13 wherein the harmonic transposition by phase-vocoder frequency spreading is performed with an estimated complexity at or below 4.5 million of operations per second and 3 kWords of memory.

The invention claimed is:

1. A method for performing high frequency reconstruction of an audio signal, the method comprising:

receiving an encoded audio bitstream, the encoded audio bitstream including audio data representing a lowband portion of the audio signal and high frequency reconstruction metadata, wherein the high frequency reconstruction metadata includes envelope scale factors;

decoding the audio data to generate a decoded lowband audio signal;

extracting from the encoded audio bitstream the high frequency reconstruction metadata, the high frequency reconstruction metadata including operating parameters for a high frequency reconstruction process, the operating parameters including a patching mode parameter located in a backward-compatible extension container of the encoded audio bitstream, wherein a first value of the patching mode parameter indicates spectral translation and a second value of the patching mode parameter indicates harmonic transposition by phase-vocoder frequency spreading;

filtering the decoded lowband audio signal to generate a filtered lowband audio signal;

regenerating a highband portion of the audio signal using the filtered lowband audio signal and the high frequency reconstruction metadata, wherein the regenerating includes spectral translation if the patching mode parameter is the first value and the regenerating includes harmonic transposition by phase-vocoder frequency spreading if the patching mode parameter is the second value; and combining the filtered lowband audio signal with the regenerated highband portion to form a wideband audio signal, wherein the filtering, regenerating, and combining are performed as a post-processing operation with a delay of 3010 samples per audio channel and wherein the spectral translation comprises maintaining a ratio between tonal and noise-like components by adaptive inverse filtering.

2. The method of claim 1 wherein the harmonic transposition by phase-vocoder frequency spreading is performed with an estimated complexity at or below 4.5 million of operations per second and at or below 3 kWords of memory.

3. A non-transitory computer readable medium containing instructions that when executed by a processor perform the method of claim 1.

4. A computer program product stored in a non-transitory computer readable medium having instructions which, when executed by a computing device or system, cause said computing device or system to execute the method of claim 1.

5. An audio processing unit for performing high frequency reconstruction of an audio signal, the audio processing unit comprising:

an input interface for receiving an encoded audio bitstream, the encoded audio bitstream including audio data representing a lowband portion of the audio signal and high frequency reconstruction metadata, wherein the high frequency reconstruction metadata includes envelope scale factors;

a core audio decoder for decoding the audio data to generate a decoded lowband audio signal;

a deformatter for extracting from the encoded audio bitstream the high frequency reconstruction metadata, the high frequency reconstruction metadata including operating parameters for a high frequency reconstruction process, the operating parameters including a patching mode parameter located in a backward-compatible extension container of the encoded audio bitstream, wherein a first value of the patching mode parameter indicates spectral translation and a second value of the patching mode parameter indicates harmonic transposition by phase-vocoder frequency spreading;

an analysis filterbank for filtering the decoded lowband audio signal to generate a filtered lowband audio signal; and a high frequency regenerator for reconstructing a highband portion of the audio signal using the filtered lowband audio signal and the high frequency reconstruction metadata, wherein the reconstructing includes a spectral translation if the patching mode parameter is the first value and the reconstructing includes harmonic transposition by phase-vocoder frequency spreading if the patching mode parameter is the second value; and a synthesis filterbank for combining the filtered lowband audio signal with the regenerated highband portion to form a wideband audio signal, wherein the analysis filterbank, high frequency regenerator, and synthesis filterbank are performed in a post-processor with a delay of 3010 samples per audio channel and wherein the spectral translation comprises maintaining a ratio between tonal and noise-like components by adaptive inverse filtering.

* * * * *

UNITED STATES PATENT AND TRADEMARK OFFICE
CERTIFICATE OF CORRECTION

| | | |
|---|---|---|
| PATENT NO. | : 12,296,028 B2 | Page 1 of 1 |
| APPLICATION NO. | : 18/982254 | |
| DATED | : May 13, 2025 | |
| INVENTOR(S) | : Kjoerling et al. | |

It is certified that error appears in the above-identified patent and that said Letters Patent is hereby corrected as shown below:

On the Title Page

Page 2, Column 1, Item (63) Related U.S. Application Data:
Line 5, After "17/050,664,", delete "filed as application No. PCT/US2019/029144 on Apr. 25, 2019, now Pat. No. 11,562,759." and insert --¶now Pat. No. 11,562,759, which is the 371 national stage of PCT Application No PCT/US2019/029144, which claims priority to US Provisional Patent Application No. 62/662,296.--

Signed and Sealed this
Sixteenth Day of September, 2025

Coke Morgan Stewart
*Acting Director of the United States Patent and Trademark Office*